(12) United States Patent
Fishman et al.

(10) Patent No.: US 6,558,932 B1
(45) Date of Patent: May 6, 2003

(54) GRIDLOCK NUCLEIC ACID MOLECULES, POLYPEPTIDES, AND DIAGNOSTIC AND THERAPEUTIC METHODS

(75) Inventors: Mark C. Fishman, Newton Center, MA (US); Tao P. Zhong, Belmont, MA (US)

(73) Assignee: The General Hospital Corp., Boston, MA (US)

( * ) Notice: Subject to any disclaimer, the term of this patent is extended or adjusted under 35 U.S.C. 154(b) by 0 days.

(21) Appl. No.: 09/705,534

(22) Filed: Nov. 3, 2000

Related U.S. Application Data
(60) Provisional application No. 60/163,903, filed on Nov. 5, 1999.

(51) Int. Cl.$^7$ .............................. C12N 9/00; C07K 17/00
(52) U.S. Cl. ........................................ 435/183; 530/350
(58) Field of Search ........................... 530/350; 435/183

(56) References Cited

PUBLICATIONS

Leimeister et al. Hey genes: a novel subfamily of hairy–and enhancer of split related genes specifically expressed during mouse embryogenesis Mechanisms of Deveolpment 85 1999 173–177.*

Chin et al., "Cardiovascular Basic Helix Loop Helix Factor 1, a Novel Transcriptional Repressor Expressed Preferentially in the Developing and Adult Cardiovascular System," Journal of Biological Chemistry 275:6381–6387 (2000).

Leimeister et al., "Hey Genes: A Novel Subfamily of Hairy–and Enhancer of Split Related Genes Specifically Expressed During Mouse Embryogenesis," Mechanisms of Development 85:173–177 (1999).

Stainier et al., "Mutations Affecting the Formation and Function of the Cardiovascular System in the Zebrafish Embryo," Development 123:285–292 (1995).

Weinstein et al., "Gridlock, a Localized Heritable Vascular Patterning Defect in the Zebrafish," Nature Medicine 11:1143–1147 (1995).

Zhong et al., "Gridlock, an HLH Gene Required for Assembly of the Aorta in Zebrafish," Science 287:1820–1824 (2000).

Fisher et al., "The WRPW Motif of the Hairy–Related Basic Helix–Loop–Helix Repressor Proteins Acts as a 4–Amino–Acid Transcription Repression and Protein–Protein Interaction Domain," Molecular and Cellular Biology 16:2670–2677 (1996).

Kokubo et al., "Identification and Expression of a Novel Family of bHLH cDNAs Related to Drosophila Hairy and Enhancer of Split," Biochemical and Biophysical Research Communications 260:459–465 (1999).

\* cited by examiner

*Primary Examiner*—Remy Yucel
*Assistant Examiner*—Konstantina Katcheves
(74) *Attorney, Agent, or Firm*—Clark & Elbing LLP

(57) ABSTRACT

The invention provides a novel gene, gridlock, and its encoded protein. gridlock plays a role in vascular development and modeling, and a mutation in gridlock has been associated with an aortic arch disease, coarctation. Thus, gridlock nucleic acid molecules and polypeptides can be used in methods of diagnosing, treating, and preventing gridlock-related diseases and conditions, such as aortic arch diseases.

7 Claims, 7 Drawing Sheets

(4 of 7 Drawing Sheet(s) Filed in Color)

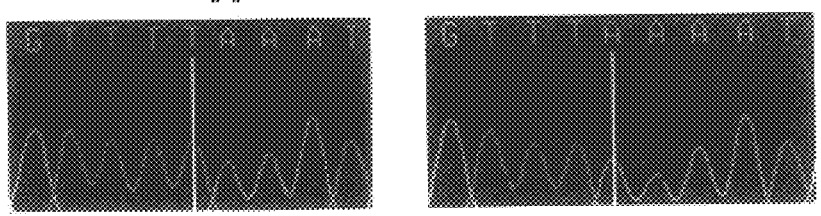

FIG. 2D

*grl* phenotype

*grl* genotype

1. AGCGTTTTAAATGTT
2. AGCGTTTTAAATGTT
3. AGCGTTTTAAATGTT
4. AGCGTTTTAAATGTT

*grl* phenotype

*grl* genotype

1. AGCGTTT AAAATGTT
2. AGCGTTT AAAATGTT
3. AGCGTTT AAAATGTT
4. AGCGTTT AAAATGTT

*grl* phenotype

*grl* genotype

1. AGCGTTT AAAATGTT
2. AGCGTTT AAAATGTT
3. AGCGTTT AAAATGTT
4. AGCGTTT AAAATGTT

Fig. 5A

GRL/human/1598 bp.
tcggcgtccgagcttccggccgggctgtgccccgcgcggtcttcgccgggatgaagcgcccctgcgaggagacgacctcc
gagagcgacatggacgagaccatcgacgtggggagcgagaacaattactcggggcaaagtactagctctgtgattagatt
gaattctccaacaacaacatctcagattatggcaagaaagaaaaggagagggattatagagaaaaggcgtcgggatcgga
taaataacagtttatctgagttgagaagacttgtgccaactgcttttgaaaaacaaggatctgcaaagttagaaaaagct
gaaatattgcaaatgacagtggatcatttgaagatgcttcaggcaacaggggggtaaaggctactttgacgcacacgctct
tgccatggacttcatgagcataggattccgagagtgcctaacagaagttgcgcggtacctgagctccgtggaaggcctgg
actcctcggatccgctgcgggtgcggcttgtgtctcatctcagcacttgcgccacccagcgggaggcggcggccatgaca
tcctccatggcccaccaccatcatccgctccacccgcatcactgggccgccgccttccaccacctgcccgcagccctgct
ccagcccaacggcctccatgcctcagagtcaaccccttgtcgcctctccacaacttcagaagtgcctcctgcccacggct
ctgctctcctcacggccacgtttgcccatgcggattcagccctccgaatgccatccacggcagcgtcgcccccctgcgtg
ccacctctctccacctctctcttgtccctctctgccaccgtccacgccgcagccgcagcagccaccgcggctgcacacag
cttccctctgtccttcgcgggggcattccccatgcttcccccaaacgcagcagcagcagtggccgcggccaacgccatca
gcccgcccttgtcagtatcagccacgtccagtcctcagcagaccagcagtggaacaaacaataaaccttaccgaccctgg
gggacagaagttggagcttttaaattttcttgaacttcttgcaatagtaactgaatgtcctccatttcagagtcagct
taaaacctctgcaccctgaaggtagccatacagatgccgacagatccacaaaggaacaataaagctatttgagacacaaa cctcacgagtggaaatgtggtattctctttttttctctcccttttttgtttggttcaaggcagctcggtaactgacatc
agcaacttttgaaaacttcacacttgttaccatttagaagtttcctggaaaatatatggaccgtaccatccagcagtgca
tcagtatgtctgaattggggaagtaaaatgccctgactgaattctcttgagactagatgggacatacatatatagagaga
gagtgagagagtcgtgtttcgtaagtgcctgagcttaggaagttttcttctggatatataacattgcacaagggaagacg
agtgtggaggataggttaagaaaggaaagggacagaagtcttgcaataggctgcagacattttaataccatgccagag

Fig. 5B

GRL/zebrafish/1898 bp.
ggaatgaagtttgagacctccattcgacggctcggggcgtgttttctattttttttttacggtgggtgttcccgaagcag
gacgtgggcgtgaatgtgagactgaggctccagcggttcgtgggaaaggcgctcagagagttttggtgtctgtacctgc
gcgcactgcatcatgaagcggccctgtgaggacagcacgtccgacagcgacatggatgaaaccattgatgtgggcagcgc
gaataactactctggccaaagcaatggttcatttataagatgtggctcacctacaacgacatcccaagtcatggccagaa
agaagcggagagggatcattgaaaaaagaagaagggaccggataaataatagcttatcagagttgcgtcgtctggtgcca
acagcttttgagaaacagggatctgccaagttggagaaagcggaaatattgcagatgacagtggatcatctgaagatgct
tcaggccacaggaggaaaaggatatttcgacgctcattctctggccatggacttcttgagcattggcttccgggagtgtc
tgactgaagtggccaggtatttgagctctgtggaaggcctggactccagcgaccctctccgtgtccgtctggtttctcac
ctcagcagctgtgcttcgcagagggaagcagccgccatgaccacatccatagcccatcaccagcaggcccttcacccgca
ccactgggctgccgctttgcatcccattcctgctgcgttcctgcagcagagcggacttccctcctcagagagctcctccg
gcaggctgtctgaggctcctcaaagaggtgcagcccttttctcccatagtgactcggcactcagagcgccctctactgga
agtgtggctccttgcgtgccaccgctgtccacttctctgctttcgttatcagcgaccgttcacgcagcagctgctgcagc
tgcagctcaaaccttccctctatcatttcccgctggattcccactcttcagccccagcgttacagcatcttcagtggctt
cttccaccgtgagctcttccgtttccacatccaccacatcccaacagagcagcgggagcaacagtaaaccataccgaccg
tggggaactgaagtgggagcgttttaaatgttggatttaaatgttggacgtcttccatgctttgtacataaaggaaagca
gcggctattgtgcctgcttcggtcagcagcatgggcttttgtcttcctctacacttgtgcacatatgcagcgtcaaactt
aagccaacattctgggaagaaaagaaagagttttttacacgtcgcactgtgttggaaaccgtaaaggaagtttgtttctgt
tttaacagtgcctgcataaacactgctaacatgctgcatttgagatgtatgctttgatatcatctgacttccacaaacac
ccaacagcagctttagagtgaacagcttgttctgaaacaaaccaaagttttgcagataatcactaaagtgaggtgtttgt
ttttttatctctgatttaacaatccagtttgtaaatctgtacatgtgtaagattgtaactagagtttatattgaaattag
ttcattggtatgatgcacttcaatcactactgtttgtttggggggagacaggatcttctccgatttatacaataggccta
ctgaagttgttttttaaaataacattcactaatactcatgtgagattttctactactgtaactgtgttaataaccacc
ctctgtaagatgtaaccttttcctatgcaaaaaaacaaatgtccctcaagaacgaactgagtgtgttttgttttcattct
gacacacgctaataaaaccatccttccactagccttcaccacaacacatcgtggaatg

SEQUENCE LISTING

```
<160> NUMBER OF SEQ ID NOS:  4

<210> SEQ ID NO 1
<211> LENGTH: 1598
<212> TYPE: DNA
<213> ORGANISM: Homo sapiens

<400> SEQUENCE: 1
tcggcgtccg agcttccggc cgggctgtgc cccgcgcggt cttcgccggg atgaagcgcc      60
cctgcgagga gacgacctcc gagagcgaca tggacgagac catcgacgtg gggagcgaga     120
acaattactc ggggcaaagt actagctctg tgattagatt gaattctcca acaacaacat     180
ctcagattat ggcaagaaag aaaaggagag ggattataga gaaaaggcgt cgggatcgga     240
taaataacag tttatctgag ttgagaagac ttgtgccaac tgcttttgaa aaacaaggat     300
ctgcaaagtt agaaaaagct gaaatattgc aaatgacagt ggatcatttg aagatgcttc     360
```

-continued

```
aggcaacagg gggtaaaggc tactttgacg cacacgctct tgccatggac ttcatgagca    420
taggattccg agagtgccta acagaagttg cgcggtacct gagctccgtg aaggcctgg     480 actcctcgga tccgctgcgg gtgcggcttg tgtctcatct cagcacttgc gccacccagc    540
gggaggcggc ggccatgaca tcctccatgg cccaccacca tcatccgctc acccgcatc     600 actgggccgc cgccttccac cacctgcccg cagccctgct ccagcccaac ggcctccatg    660
cctcagagtc aacccttgt cgcctctcca caacttcaga agtgcctcct gcccacggct     720
ctgctctcct cacggccacg tttgcccatg cggattcagc cctccgaatg ccatccacgg    780
gcagcgtcgc ccctgcgtg ccacctctct ccacctctct cttgtccctc tctgccaccg     840
tccacgccgc agccgcagca gccaccgcgg ctgcacacag cttccctctg tccttcgcgg    900
gggcattccc catgcttccc ccaaacgcag cagcagcagt ggccgcggcc acagccatca    960
gcccgccctt gtcagtatca gccacgtcca gtcctcagca gaccagcagt ggaacaaaca   1020 ataaaccta ccgaccctgg gggacagaag ttggagcttt ttaaattttt cttgaacttc     1080
ttgcaatagt aactgaatgt cctccatttc agagtcagct taaaacctct gcaccctgaa    1140
ggtagccata cagatgccga cagatccaca aaggaacaat aaagctattt gagacacaaa    1200
cctcacgagt ggaaatgtgg tattctcttt tttttctctc ccttttttgt ttggttcaag    1260
gcagctcggt aactgacatc agcaactttt gaaaacttca cacttgttac catttagaag    1320
tttcctggaa aatatatgga ccgtaccatc cagcagtgca tcagtatgtc tgaattgggg    1380
aagtaaaatg ccctgactga attctcttga gactagatgg gacatacata tatagagaga    1440
gagtgagaga gtcgtgtttc gtaagtgcct gagcttagga agttttcttc tggatatata    1500
acattgcaca agggaagacg agtgtggagg ataggttaag aaaggaaagg gacagaagtc    1560
ttgcaatagg ctgcagacat tttaatacca tgccagag                             1598
```

<210> SEQ ID NO 2
<211> LENGTH: 337
<212> TYPE: PRT
<213> ORGANISM: Homo sapiens

<400> SEQUENCE: 2

```
Met Lys Arg Pro Cys Glu Glu Thr Thr Ser Glu Ser Asp Met Asp Glu
 1               5                  10                  15

Thr Ile Asp Val Gly Ser Glu Asn Asn Tyr Ser Gly Gln Ser Thr Ser
             20                  25                  30

Ser Val Ile Arg Leu Asn Ser Pro Thr Thr Thr Ser Gln Ile Met Ala
         35                  40                  45

Arg Lys Lys Arg Arg Gly Ile Ile Glu Lys Arg Arg Arg Asp Arg Ile
     50                  55                  60

Asn Asn Ser Leu Ser Glu Leu Arg Arg Leu Val Pro Thr Ala Phe Glu
 65                  70                  75                  80

Lys Gln Gly Ser Ala Lys Leu Glu Lys Ala Glu Ile Leu Gln Met Thr
                 85                  90                  95

Val Asp His Leu Lys Met Leu Gln Ala Thr Gly Gly Lys Gly Tyr Phe
            100                 105                 110

Asp Ala His Ala Leu Ala Met Asp Phe Met Ser Ile Gly Phe Arg Glu
        115                 120                 125

Cys Leu Thr Glu Val Ala Arg Tyr Leu Ser Ser Val Glu Gly Leu Asp
    130                 135                 140

Ser Ser Asp Pro Leu Arg Val Arg Leu Val Ser His Leu Ser Thr Cys
```

```
            145                 150                 155                 160
Ala Thr Gln Arg Glu Ala Ala Met Thr Ser Ser Met Ala His His
                165                 170                 175
His His Pro Leu His Pro His His Trp Ala Ala Ala Phe His His Leu
            180                 185                 190
Pro Ala Ala Leu Leu Gln Pro Asn Gly Leu His Ala Ser Glu Ser Thr
            195                 200                 205
Pro Cys Arg Leu Ser Thr Thr Ser Glu Val Pro Pro Ala His Gly Ser
        210                 215                 220
Ala Leu Leu Thr Ala Thr Phe Ala His Ala Asp Ser Ala Leu Arg Met
225                 230                 235                 240
Pro Ser Thr Gly Ser Val Ala Pro Cys Val Pro Pro Leu Ser Thr Ser
                245                 250                 255
Leu Leu Ser Leu Ser Ala Thr Val His Ala Ala Ala Ala Ala Thr
            260                 265                 270
Ala Ala Ala His Ser Phe Pro Leu Ser Phe Ala Gly Ala Phe Pro Met
            275                 280                 285
Leu Pro Pro Asn Ala Ala Ala Val Ala Ala Ala Thr Ala Ile Ser
        290                 295                 300
Pro Pro Leu Ser Val Ser Ala Thr Ser Ser Pro Gln Gln Thr Ser Ser
305                 310                 315                 320
Gly Thr Asn Asn Lys Pro Tyr Arg Pro Trp Gly Thr Glu Val Gly Ala
                325                 330                 335
Phe

<210> SEQ ID NO 3
<211> LENGTH: 1898
<212> TYPE: DNA
<213> ORGANISM: Danio rerio

<400> SEQUENCE: 3
ggaatgaagt ttgagacctc cattcgacgg ctcggggcgt gttttctatt ttttttttac    60
ggtgggtgtt cccgaagcag gacgtgggcg tgaatgtgag actgaggctc cagcggttcg   120
tgggaaaggc gctcagagag ttttttggtgt ctgtacctgc gcgcactgca tcatgaagcg   180
gccctgtgag gacagcacgt ccgacagcga catggatgaa accattgatg tgggcagcca   240
gaataactac tctggccaaa gcaatggttc atttataaga tgtggctcac ctacaacgac   300
atcccaagtc atgccagaa agaagcggag agggatcatt gaaaaagaa gaagggaccg    360
gataaataat agcttatcag agttgcgtcg tctggtgcca acagcttttg agaaacaggg   420
atctgccaag ttgagaaag cggaaatatt gcagatgaca gtggatcatc tgaagatgct    480
tcaggccaca ggaggaaaag gatatttcga cgctcattct ctggccatgg acttcttgag   540
cattggcttc cggagtgtc tgactgaagt ggccaggtat ttgagctctg tggaaggcct    600
ggactccagc gaccctctcc gtgtccgtct ggtttctcac ctcagcagct gtgcttcgca   660
gagggaagca gccgccatga ccacatccat agccatcac cagcaggccc ttcacccgca    720
ccactgggct gccgctttgc atcccattcc tgctgcgttc ctgcagcaga gcggacttcc   780
ctcctcagag agctcctccg gcaggctgtc tgaggctcct caaagaggtg cagccctttt   840
ctcccatagt gactcggcac tcagagcgcc ctctactgga agtgtggctc cttgcgtgcc   900
accgctgtcc acttctctgc tttcgttatc agcgaccgtt cacgcagcag ctgctgcagc   960
tgcagctcaa accttccctc tatcatttcc cgctggattc ccactcttca gccccagcgt  1020
```

-continued

```
tacagcatct tcagtggctt cttccaccgt gagctcttcc gtttccacat ccaccacatc    1080
ccaacagagc agcgggagca acagtaaacc ataccgaccg tggggaactg aagtgggagc    1140
gttttaaatg ttggatttaa atgttggacg tcttccatgc tttgtacata aggaaagca    1200 gcggctattg tgcctgcttc ggtcagcagc atgggctttt gtcttcctct acacttgtgc    1260
acatatgcag cgtcaaactt aagccaacat tctgggaaga aaagaaagag tttttacacg    1320
tcgcactgtg ttggaaaccg taaggaagt ttgtttctgt tttaacagtg cctgcataaa    1380
cactgctaac atgctgcatt tgagatgtat gctttgatat catctgactt ccacaaacac    1440
ccaacagcag ctttagagtg aacagcttgt tctgaaacaa accaaagttt tgcagataat    1500
cactaaagtg aggtgtttgt ttttttatct ctgatttaac aatccagttt gtaaatctgt    1560
acatgtgtaa gattgtaact agagtttata ttgaaattag ttcattggta tgatgcactt    1620
caatcactac tgtttgtttg ggggagaca ggatcttctc cgatttatac aataggccta    1680
ctgaagttgt ttttttaaaa taacattcac taatactcat gtgagatttt tctactactg    1740
taactgtgtt aataaccacc ctctgtaaga tgtaaccttt tcctatgcaa aaaacaaat    1800 gtccctcaag aacgaactga gtgtgttttg ttttcattct gacacacgct aataaaacca    1860
tccttccact agccttcacc acaacacatc gtggaatg                           1898
```

<210> SEQ ID NO 4
<211> LENGTH: 324
<212> TYPE: PRT
<213> ORGANISM: Danio rerio

<400> SEQUENCE: 4

```
Met Lys Arg Pro Cys Glu Asp Ser Thr Ser Asp Ser Asp Met Asp Glu
  1               5                  10                  15

Thr Ile Asp Val Gly Ser Gln Asn Asn Tyr Ser Gly Gln Ser Asn Gly
             20                  25                  30

Ser Phe Ile Arg Cys Gly Ser Pro Thr Thr Ser Gln Val Met Ala
         35                  40                  45

Arg Lys Lys Arg Arg Gly Ile Ile Glu Lys Arg Arg Asp Arg Ile
     50                  55                  60

Asn Asn Ser Leu Ser Glu Leu Arg Arg Leu Val Pro Thr Ala Phe Glu
 65                  70                  75                  80

Lys Gln Gly Ser Ala Lys Leu Glu Lys Ala Glu Ile Leu Gln Met Thr
                 85                  90                  95

Val Asp His Leu Lys Met Leu Gln Ala Thr Gly Gly Lys Gly Tyr Phe
            100                 105                 110

Asp Ala His Ser Leu Ala Met Asp Phe Leu Ser Ile Gly Phe Arg Glu
        115                 120                 125

Cys Leu Thr Glu Val Ala Arg Tyr Leu Ser Ser Val Glu Gly Leu Asp
    130                 135                 140

Ser Ser Asp Pro Leu Arg Val Arg Leu Val Ser His Leu Ser Ser Cys
145                 150                 155                 160

Ala Ser Gln Arg Glu Ala Ala Ala Met Thr Thr Ser Ile Ala His His
                165                 170                 175

Gln Gln Ala Leu His Pro His Trp Ala Ala Ala Leu His Pro Ile
            180                 185                 190

Pro Ala Ala Phe Leu Gln Gln Ser Gly Leu Pro Ser Ser Glu Ser Ser
        195                 200                 205

Ser Gly Arg Leu Ser Glu Ala Pro Gln Arg Gly Ala Ala Leu Phe Ser
    210                 215                 220
```

-continued

```
His Ser Asp Ser Ala Leu Arg Ala Pro Ser Thr Gly Ser Val Ala Pro
225                 230                 235                 240

Cys Val Pro Pro Leu Ser Thr Ser Leu Leu Ser Leu Ser Ala Thr Val
                245                 250                 255

His Ala Ala Ala Ala Ala Ala Ala Gln Thr Phe Pro Leu Ser Phe
                260                 265                 270

Pro Ala Gly Phe Pro Leu Phe Ser Pro Ser Val Thr Ala Ser Ser Val
            275                 280                 285

Ala Ser Ser Thr Val Ser Ser Ser Val Ser Thr Ser Thr Thr Ser Gln
    290                 295                 300

Gln Ser Ser Gly Ser Asn Ser Lys Pro Tyr Arg Pro Trp Gly Thr Glu
305                 310                 315                 320

Val Gly Ala Phe
```

GRIDLOCK NUCLEIC ACID MOLECULES, POLYPEPTIDES, AND DIAGNOSTIC AND THERAPEUTIC METHODS This application claims the benefit of Provisional Application No. 60/163,903, filed Nov. 5, 1999.

Statement as to Federally Sponsored Research

This research has been sponsored, in part, by grant numbers HL07208, RO1-RR0888, RO1-DK55383, and RO-HL49579 from the National Institutes of Health. The government may have certain rights in the invention.

FIELD OF THE INVENTION

This invention relates to cardiovascular diseases.

Background of the Invention

The vascular system contains vessels that are morphologically and functionally distinct. For example, arteries carry oxygenated blood at high pressure from the heart, while veins serve as capacitance vessels for blood return. While some of the differences within the vascular system occur after the onset of function, a complete vascular loop, formed by the trunk artery and vein, is required to accommodate the output of the first heart beat. The major trunk vessels, the aorta and the axial vein, of vertebrate embryos are formed by the coalescence of scattered mesodermal angioblasts into simple endothelial tubes by a process termed "vasculogenesis," which is distinguished from "angiogenesis," the formation of vessels by sprouting and remodeling (Fishman, "Assembly of blood vessels in the embryos," Lippincott-Raven Publishers, Philadelphia, 1996; Folkman et al., *Cell* 87:1153–1155, 1996; Risau, *Nature* 386:671–674, 1997; Yancopolos et al., *Cell* 93:661–664, 1998).

The aorta, the main trunk of the systemic arterial network, is subject to several congenital and acquired disorders, that may lead to severe complications in infancy and adulthood. Coarctation of the aorta is one of the most common human congenital cardiovascular diseases. In coarctation, a discrete, localized vascular malformation partially obstructs the descending aorta, the major artery to the body, and most frequently occurs distal to the origins of vessels supplying the head and arms. Its effects often become more physiologically severe at birth, when closure of the ductus can exacerbate the restriction to aortic blood flow. As a consequence of coarctation, affected individuals suffer from high blood pressure in the upper extremities and head, and from low pressure in the trunk and legs. Survival often depends on the development of collateral blood vessels, which facilitate blood circulation in a manner so as to bypass the lesion.

Another serious cardiovascular disease that affects large numbers of individuals is atherosclerosis. This condition is characterized by the deposition of lipids in the intima of large and medium-sized arteries. Such deposits are associated with fibrosis and calcification.

The gridlock mutation ($grl^{m145}$) is a recessive mutation that was identified in the zebrafish system and that causes a focal vascular malformation resembling coarctation of the aorta in humans. In $grl^{m145}$ mutant embryos, fluorescent dextran injected into the heart, to outline patent vessels, is blocked at the origin of the dorsal aorta at the region where the two anterior dorsal aortae merge to form the single aorta of the trunk. The fluorescent beads circulated normally in the head (Weinstein et al., *Nature Medicine* 1:1143–1147, 1995). Thus, the grl mutant embryos lack circulation to the trunk.

SUMMARY OF THE INVENTION

The invention provides a novel gene, gridlock, and its encoded protein. gridlock plays a role in vascular development and modeling, and a mutation in gridlock has been associated with an aortic arch disease, coarctation. Thus, gridlock nucleic acid molecules and polypeptides can be used in methods of diagnosing, treating, and preventing gridlock-related diseases and conditions, such as aortic arch diseases.

In one aspect, the invention provides a substantially pure gridlock polypeptide. In preferred embodiments of this aspect, the gridlock polypeptide includes the amino acid sequence of SEQ ID NO:2 or SEQ ID NO:4, or includes an amino acid sequence that is substantially identical to the amino acid sequence of SEQ ID NO:2 or SEQ ID NO:4. In other preferred embodiments of this aspect, the polypeptide is derived from a mammal, e.g., a human.

In another aspect, the invention provides a substantially pure nucleic acid molecule, e.g., DNA, including a sequence encoding a gridlock polypeptide. In a preferred embodiment of this aspect, the nucleic acid molecule encodes a human gridlock polypeptide. In other preferred embodiments of this aspect, the nucleic acid molecule encodes a polypeptide including the amino acid sequence of SEQ ID NO:2 or SEQ ID NO:4, or encodes a polypeptide including an amino sequence that is substantially identical to the amino acid sequence of SEQ ID NO:2 or SEQ ID NO:4. In other preferred embodiments of this aspect, the nucleic acid molecule includes a nucleotide sequence that is substantially identical to the nucleotide sequence of SEQ ID NO:1 or SEQ ID NO:3.

In a related aspect, the invention provides a nucleic acid molecule having at least 55% nucleic acid sequence identity to a sequence encoding a gridlock polypeptide or a fragment thereof, where the fragment includes at least six amino acids and the nucleic acid molecule hybridizes under high stringency conditions to at least a portion of a gridlock nucleic acid molecule, and does not hybridize under high stringency conditions to a nucleic acid molecule encoding a hairy-related protein family member. In a preferred embodiment of this aspect, the nucleic acid molecule has 100% complementarity to a nucleic acid molecule encoding a gridlock polypeptide or a fragment thereof including at least six amino acids, and the nucleic acid molecule hybridizes under high stringency conditions to at least a portion of a gridlock nucleic acid molecule, and does not hybridize under high stringency conditions to a nucleic acid molecule encoding a hairy-related protein family member.

In a related aspect, the invention provides a nucleic acid molecule including a sequence that is antisense to a gridlock coding strand or a fragment thereof. In a preferred embodiment of this aspect, the antisense sequence is specific for a mutated gridlock coding region.

In another related aspect, the invention provides a vector, e.g., a gene therapy vector including a gridlock nucleic acid molecule, and a cell including this vector.

In other aspects, the invention provides a non-human transgenic animal, e.g., a zebrafish, including a gridlock nucleic acid molecule, and a non-human animal having a knockout mutation in one or both alleles encoding a gridlock polypeptide. The invention also provides a cell from a non-human animal having a knockout mutation in one or both alleles encoding a gridlock polypeptide.

In other aspects, the invention provides a probe for analyzing the gridlock nucleic acid molecules of an animal, the probe having at least 55% nucleic acid sequence identity to a sequence encoding a gridlock polypeptide or a fragment thereof. The fragment includes at least six amino acids and the probe hybridizes under high stringency conditions to at least a portion of a gridlock nucleic acid molecule, and does not hybridize under high stringency conditions to a nucleic acid molecule encoding a hairy-related protein family member. In a preferred embodiment, the probe has 100% complementarity to a nucleic acid molecule encoding a gridlock polypeptide or a fragment thereof including at least six amino acids, and the probe hybridizes under high stringency conditions to at least a portion of a gridlock nucleic acid molecule, and does not hybridize under high stringency conditions to a nucleic acid molecule encoding a hairy-related protein family member.

In another aspect, the invention provides an antibody that specifically binds to a gridlock polypeptide, e.g., a polypeptide including the amino acid sequence of SEQ ID NO:2 or SEQ ID NO:4.

In another aspect, the invention provides a method of detecting the presence of a gridlock polypeptide in a sample. The method involves contacting the sample with an antibody that specifically binds to a gridlock polypeptide and assaying for binding of the antibody to the polypeptide.

In another aspect, the invention provides a method of detecting the presence of a mutant gridlock polypeptide in a sample. The method involves contacting the sample with an antibody that specifically binds to a mutant gridlock polypeptide and assaying for binding of the antibody to the mutant polypeptide.

In another aspect, the invention provides a method of diagnosing an increased likelihood of developing a gridlock-related disease or condition in a test subject. The method involves analyzing nucleic acid molecules of the test subject to determine whether the test subject contains a mutation in a gridlock gene. The presence of the mutation is an indication that the test subject has an increased likelihood of developing a gridlock-related disease. In preferred embodiments of this aspect, the test subject is a mammal, e.g, a human. In other preferred embodiments of this aspect, the method includes the step of using nucleic acid molecule primers specific for the gridlock gene for nucleic acid molecule amplification by the polymerase chain reaction, or includes the step of sequencing gridlock nucleic acid molecules from the test subject. In another preferred embodiment of this aspect, the analyzing is carried out by restriction fragment length polymorphism (RFLP) analysis. In another preferred embodiment of this aspect, the disease or condition is coarctation of the aorta, interrupted aortic arch disease, or atherosclerosis.

In another aspect, the invention provides a kit for the analysis of a gridlock nucleic acid molecule. The kit includes a nucleic acid molecule probe for analyzing the gridlock nucleic acid molecules of a test subject.

In another aspect, the invention provides a kit for the analysis of a gridlock nucleic acid molecule. The kit includes antibodies for analyzing the gridlock protein of a test subject.

In another aspect, the invention provides a method for preventing or ameliorating the effect of a gridlock deficiency by administering to a subject having a gridlock deficiency an expression vector including a nucleic acid molecule encoding a functional gridlock polypeptide. The nucleic acid molecule is operably linked to a promoter and the gridlock polypeptide is sufficient to prevent or ameliorate the effect of the gridlock deficiency.

In a related aspect, the invention provides a method for preventing or ameliorating the effect of a gridlock deficiency by administering a functional gridlock polypeptide to a subject having a gridlock deficiency. The gridlock polypeptide is sufficient to prevent or ameliorate the effect of the gridlock deficiency.

In a further aspect, the invention provides a method for preventing or ameliorating the effect of a gridlock excess by administering an antisense gridlock molecule to a subject having a gridlock excess. The antisense gridlock molecule is sufficient to prevent or ameliorate the effect of the gridlock excess.

In a related aspect, the invention provides a method for preventing or ameliorating the effect of a gridlock excess by administering a gridlock antibody to a subject having a gridlock excess. The gridlock antibody is sufficient to prevent or ameliorate the effect of the gridlock excess.

In another aspect, the invention provides a method for identifying a compound that modulates the expression or activity of a gridlock nucleic acid molecule or polypeptide. The method involves contacting the gridlock nucleic acid molecule or polypeptide with the compound, and determining the effect of the compound on the gridlock expression or activity.

By "polypeptide" or "polypeptide fragment" is meant a chain of two or more amino acids, regardless of any post-translational modification (e.g., glycosylation or phosphorylation), constituting all or part of a naturally or non-naturally occurring polypeptide. By "post-translational modification" is meant any change to a polypeptide or polypeptide fragment during or after synthesis. Post-translational modifications can be produced naturally (such as during synthesis within a cell) or generated artificially (such as by recombinant or chemical means). A "protein" can be made up of one or more polypeptides.

By "gridlock," "gridlock protein," or "gridlock polypeptide" is meant a polypeptide that has at least 45%, preferably at least 60%, more preferably at least 75%, and most preferably at least 90% amino acid sequence identity to the sequence of the human or the zebrafish gridlock polypeptides shown in FIG. 2 (SEQ ID NO:2 and SEQ ID NO:4, respectively). A polypeptide having at least 85% amino acid identity to the bHLH or at least 55% amino acid identity to the Orange domains of the human or the zebrafish gridlock polypeptides shown in FIG. 2 (SEQ ID NO:2 and SEQ ID NO:4, respectively) can be considered a gridlock polypeptide. Most preferably, such a polypeptide has at least 95% amino acid identity in the bHLH domain or at least 90% amino acid identity in the Orange domain to the human or the zebrafish gridlock polypeptides shown in FIG. 2 (SEQ ID NO:2 and SEQ ID NO:4, respectively). Polypeptide products from splice variants of gridlock gene sequences and gridlock genes containing mutations (e.g., the $grl^{m145}$ mutation) are also included in this definition. Preferably, a gridlock polypeptide contains a "YRPW" motif. A gridlock polypeptide as defined herein plays a role in vascular development and modeling. It can be used as an early marker of vasculogenesis or angioblast cell fate determination, as well as an artery-specific, for example, an aorta-specific, marker later in development or in adults.

By a "gridlock nucleic acid molecule" is meant a nucleic acid molecule, such as a genomic DNA, cDNA, or RNA (e.g., mRNA) molecule, that encodes gridlock, a gridlock protein, a gridlock polypeptide, or a portion thereof, as defined above.

The term "identity" is used herein to describe the relationship of the sequence of a particular nucleic acid molecule or polypeptide to the sequence of a reference molecule of the same type. For example, if a polypeptide or nucleic acid molecule has the same amino acid or nucleotide residue at a given position, compared to a reference molecule to which it is aligned, there is said to be "identity" at that position. The level of sequence identity of a nucleic acid molecule or a polypeptide to a reference molecule is typically measured using sequence analysis software with the default parameters specified therein, such as the introduction of gaps to achieve an optimal alignment (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, or other modifications. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine.

A nucleic acid molecule or polypeptide is said to be "substantially identical" to a reference molecule if it exhibits, over its entire length, at least 51%, preferably at least 55%, 60%, or 65%, and most preferably 75%, 85%, 90%, or 95% identity to the sequence of the reference molecule. For polypeptides, the length of comparison sequences is at least 16 amino acids, preferably at least 20 amino acids, more preferably at least 25 amino acids, and most preferably at least 35 amino acids. For nucleic acid molecules, the length of comparison sequences is at least 50 nucleotides, preferably at least 60 nucleotides, more preferably at least 75 nucleotides, and most preferably at least 110 nucleotides.

A gridlock nucleic acid molecule or gridlock polypeptide is "analyzed" or subject to "analysis" if a test procedure is carried out on it that allows the determination of its biological activity or whether it is wild type or mutated. For example, one can analyze the gridlock genes of an animal (e.g., a human or a zebrafish) by amplifying genomic DNA of the animal using the polymerase chain reaction, and then determining whether the amplified DNA contains a mutation, e.g., by nucleotide sequence or restriction fragment analysis.

By "probe" or "primer" is meant a single-stranded DNA or RNA molecule of defined sequence that can base pair to a second DNA or RNA molecule that contains a complementary sequence ("target"). The stability of the resulting hybrid depends upon the extent of the base pairing that occurs. This stability is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are well known to those skilled in the art. Probes or primers specific for gridlock nucleic acid molecules, preferably, have greater than 45% sequence identity, more preferably at least 55–75% sequence identity, still more preferably at least 75–85% sequence identity, yet more preferably at least 85–99% sequence identity, and most preferably 100% sequence identity to the sequences designated as SEQ ID NO:1 or SEQ ID NO:3. Probes can be detectably-labeled, either radioactively or non-radioactively, by methods that are well-known to those skilled in the art. Probes can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are well known to those skilled in the art.

A molecule, e.g., an oligonucleotide probe or primer, a gene or fragment thereof, a cDNA molecule, a polypeptide, or an antibody, can be said to be "detectably-labeled" if it is marked in such a way that its presence can be directly identified in a sample. Methods for detectably-labeling molecules are well known in the art and include, without limitation, radioactive labeling (e.g., with an isotope, such as $^{32}P$ or $^{35}S$) and nonradioactive labeling (e.g., with a fluorescent label, such as fluorescein).

By a "substantially pure polypeptide" is meant a polypeptide (or a fragment thereof) that has been separated from proteins and organic molecules that naturally accompany it. Typically, a polypeptide is substantially pure when it is at least 60%, by weight, free from the proteins and naturally-occurring organic molecules with which it is naturally associated. Preferably, the polypeptide is a gridlock polypeptide that is at least 75%, more preferably at least 90%, and most preferably at least 99%, by weight, pure. A substantially pure gridlock polypeptide can be obtained, for example, by extraction from a natural source (e.g., isolated aorta or vascular tissue), by expression of a recombinant nucleic acid molecule encoding a gridlock polypeptide, or by chemical synthesis. Purity can be measured by any appropriate method, e.g., by column chromatography, polyacrylamide gel electrophoresis, or HPLC analysis.

A polypeptide is substantially free of naturally associated components when it is separated from those proteins and organic molecules that accompany it in its natural state. Thus, a protein that is chemically synthesized or produced in a cellular system different from the cell in which it is naturally produced is substantially free from its naturally associated components. Accordingly, substantially pure polypeptides not only include those derived from eukaryotic organisms, but also those synthesized in *E. coli* or other prokaryotes.

An antibody is said to "specifically bind" to a polypeptide if it recognizes and binds to the polypeptide (e.g., a gridlock polypeptide), but does not substantially recognize and bind to other molecules (e.g., non-gridlock related polypeptides) in a sample, e.g., a biological sample, that naturally includes the polypeptide.

By "high stringency conditions" is meant conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8× SSC, 0.2 M Tris-Cl, pH 7.6, 1× Denhardt's solution, 10% dextran sulfate, and 0.1% SDS, at a temperature of 42° C. (These are typical conditions for high stringency northern or Southern hybridizations.) High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually 16 nucleotides or longer for PCR or sequencing and 40 nucleotides or longer for in situ hybridization). The high stringency conditions used in these techniques are well known to those skilled in the art of molecular biology, and examples of them can be found, for example, in Ausubel et al., *Current Protocols in Molecular Biology,* John Wiley & Sons, New York, N.Y., 1998, which is hereby incorporated by reference.

By a "transgene" is meant a DNA molecule that is inserted by artifice into a cell (e.g., the nuclear genome of a cell), and is incorporated into the genome of an organism that develops from the cell. Such a transgene can be partly or entirely heterologous (i.e., foreign) to the transgenic organism, or can be a gene that is homologous to an endogenous gene of the organism. An organism or animal (e.g., a mammal, such as a mouse, rat, or goat) can be said to be "transgenic" if it developed from a cell that had a transgene inserted into it by artifice.

By a "knockout mutation" is meant an artificially-induced alteration in a nucleic acid molecule (created by recombinant DNA technology or deliberate exposure to a mutagen) that reduces the biological activity of the polypeptide normally encoded therefrom by at least 80% relative to the unmutated gene. The mutation can be, without limitation, an insertion, deletion, frameshift mutation, or a missense mutation. A "knockout animal" is preferably a mammal, and more preferably a mouse, containing a knockout mutation, as defined above.

By "transformation" is meant any method for introducing foreign molecules (e.g., nucleic acid molecules) into a cell. Lipofection, DEAE-dextran-mediated transfection, microinjection, protoplast fusion, calcium phosphate precipitation, retroviral delivery, electroporation, and biolistic transformation are just a few of the many transformation methods that are well known to those skilled in the art that can be used in the invention. For example, biolistic transformation is a method for introducing foreign molecules into a cell using velocity-driven microprojectiles such as tungsten or gold particles. Such methods can include helium-driven, air-driven, and gunpowder-driven techniques. Biolistic transformation can be applied to the transformation or transfection of a wide variety of cell types, intracellular organelles, and intact tissues including, without limitation, mitochondria, chloroplasts, bacteria, yeast, fungi, algae, animal tissue, and cultured cells.

By a "transformed cell," "transfected cell," or "transduced cell," is meant a cell (or a descendent of a cell) into which a DNA molecule encoding a polypeptide has been introduced, by means of recombinant DNA techniques.

By a "promoter" is meant a minimal nucleic acid sequence element sufficient to direct transcription. If desired, constructs of the invention can include promoter elements that are sufficient to render promoter-dependent gene expression controllable in a cell type-specific, tissue-specific, or temporal-specific manner, or inducible by external signals or agents. Such elements can be located in the 5', 3', or intron regions of a gene.

By an "operably linked sequence" is meant that a gene and one or more regulatory sequences are connected in such a way as to permit gene expression when the appropriate molecules (e.g., transcriptional activator proteins) are bound to the regulatory sequences.

By an "antisense molecule," as used herein in reference to nucleic acid molecules, is meant a nucleic acid molecule having a sequence that is complementary to at least 75 nucleotides, and preferably at least 100, 150, or 200 nucleotides, of the coding strand of a gene, such as a gridlock gene. An antisense nucleic acid molecule can be, for example, capable of preferentially lowering the production of a mutant gridlock polypeptide encoded by a mutant gridlock gene.

By "missense mutation" is meant a substitution of one purine or pyrimidine base (i.e., A, T, G, or C) by another within a nucleic acid molecule, such that the resulting new codon encodes an amino acid that is distinct from the amino acid originally encoded by the wild type codon.

By "frameshift mutation" is meant an insertion or deletion of at least one nucleotide within a polynucleotide coding sequence. A frameshift mutation alters the codon reading frame at or downstream from the mutation site. Such a mutation results in either the substitution of an encoded wild type amino acid sequence by a novel amino acid sequence, or a premature termination of an encoded polypeptide, due to the creation of a stop codon, or both.

By "sample" is meant a tissue biopsy, amniotic fluid, cell, blood, serum, urine, stool, or other specimen obtained from a patient or test subject. The sample can be analyzed to detect a mutation in a gridlock gene, or expression levels of a gridlock gene, by methods that are known in the art. For example, methods such as sequencing, single-strand conformational polymorphism (SSCP) analysis, or restriction fragment length polymorphism (RFLP) analysis of PCR products derived from a patient sample can be used to detect a mutation in a gridlock gene; ELISA can be used to measure levels of gridlock polypeptide; and PCR can be used to measure the level of a gridlock nucleic acid molecule.

By "gridlock-related disease" or "gridlock-related condition" is meant a disease or condition that results from inappropriately high or low expression of a gridlock gene, or a mutation in a gridlock gene that alters the biological activity of a gridlock nucleic acid molecule or polypeptide. gridlock-related diseases and conditions can arise in any vascular tissue in which gridlock is expressed during pre-natal or post-natal life. gridlock-related diseases and conditions can include congenital cardiovascular diseases (e.g., congenital dysmorphogenesis) and cardiovascular disease acquired in adulthood, such as atherosclerosis. By "congenital cardiovascular disease" is meant a disease associated with the abnormal formation of the heart or blood vessels. A patient suffering from a congenital cardiovascular disease, for example, an aortic arch disease, such as interrupted aortic arch disease or coarctation of the aorta, may display constriction of the aorta.

The invention provides several advantages. For example, it provides methods and reagents that can be used in the diagnosis and treatment of diseases caused by vascular malformation or dysfunction. These disorders include congenital cardiovascular diseases, such as interrupted arch diseases, aortic arch diseases, e.g., coarctation of the aorta, and cardiovascular diseases that occur in adulthood, such as atherosclerosis, hypertension, and coronary artery disease. These disorders can be treated, using the methods described herein, in a variety of ways including, for example, small molecule therapy, gene therapy, antisense oligonucleotide therapy, and protein replacement therapy. Additionally, the nucleic acid molecules and polypeptides of the invention have diagnostic/disease management applications, for example, use as prognostic markers or predisposition indicators of cardiovascular diseases.

Other features and advantages of the invention will be apparent from the detailed description of the invention, the drawings, and the claims.

BRIEF DESCRIPTION OF THE DRAWINGS

The file of this patent contains at least one drawing executed in color. Copies of this patent with color drawing(s) will be provided by the Office upon request and payment of the necessary fee.

FIG. 2A is an amino acid sequence alignment of zebrafish grl and human grl (SEQ ID NO:2 and SEQ ID NO:4).

FIG. 2B is an amino acid sequence alignment of zebrafish and human grl, hHESR-1, mHESR-1, and dHESR-1 in the basic helix-loop-helix, Orange, and YRPW domains.

FIG. 2C is a graphical diagram of nucleic acid sequencing results, showing that the grl$^{m145}$ mutation results in a T to A transversion.

FIG. 2D is an amino acid sequence alignment of zebrafish and human grl, hHESR-1, mHESR-1, and dHESR-1 proteins.

For FIGS. 3A–3J, Dorsal is up at (B), (C), (D), (E), (F), (G), (H), and (I); anterior is to the left at (B), (C), and (J). The in situ hybridization was carried out at the 30 somite (24 hours) stage. N, notochord; da, dorsal aorta; v, axial vein.

Figure 4A:

FIG. 4A is a microangiogram showing the phenotype of wild type embryos.

Figure 4B:

FIG. 4B is a microangiogram showing the phenotype of the grl mutant.

Figure 4C:

FIG. 4C is a microangiogram showing the phenotype of a rescued grl mutant.

FIG. 5A is a DNA sequence of the human grl gene (SEQ ID NO:1)

FIG. 5B is a DNA sequence of the zebrafish grl gene (SEQ ID NO:3).

DETAILED DESCRIPTION OF THE INVENTION

The invention provides gridlock genes, which play a role in vascular development and modeling, polypeptides encoded by these genes, nucleic acid molecules related to these genes (see below), and diagnostic and therapeutic methods employing these genes, polypeptides, and nucleic acid molecules. The invention also provides methods for identifying compounds that modulate the biological activities of gridlock genes and polypeptides, and therapeutic methods employing these compounds.

The diagnostic, therapeutic, and screening methods of the invention are first described, followed by general approaches that can be used in carrying out these methods. Finally, experimental results supporting the methods of the invention are described.

Diagnostic Methods Employing gridlock Nucleic Acid Molecules, Polypeptides, and Antibodies gridlock nucleic acid molecules, polypeptides, and antibodies can be used in methods to diagnose or monitor diseases and conditions involving mutations in, or inappropriate expression of, gridlock genes. As discussed above, the gridlock mutation in zebrafish, which results in the translation of an abnormally long gridlock polypeptide, is characterized by a phenotype that is similar to that of coarctation in humans. Thus, detection of abnormalities in gridlock genes or their expression can be used in methods to diagnose, or to monitor treatment or development of, human interrupted arch or aortic arch diseases, such as coarctation. gridlock may also play a role in cardiovascular diseases other than aortic arch diseases, such as atherosclerosis, and, thus, detection of abnormalities in gridlock genes or their expression can be used in methods to diagnose and monitor these conditions as well.

The diagnostic methods of the invention can be used, for example, with patients that have an aortic arch disease, in an effort to determine its etiology, and, thus, to facilitate selection of an appropriate course of treatment. The diagnostic methods can also be used with patients that have not yet developed an aortic arch disease, but who may be at risk of developing such a disease, or with patients that are at an early stage of developing such a disease. Many aortic arch diseases occur during development, and, thus the diagnostic methods of the invention can be carried out on a fetus or embryo during development. Also, the diagnostic methods of the invention can be used in prenatal genetic screening, for example, to identify parents who may be carriers of a recessive gridlock mutation.

gridlock abnormalities that can be detected using the diagnostic methods of the invention include those characterized by, for example, (i) abnormal gridlock polypeptides (e.g., abnormally long gridlock polypeptides), (ii) gridlock genes containing mutations that result in the production of such polypeptides, and (iii) gridlock mutations that result in production of abnormal amounts of gridlock. Detection of such abnormalities, thus, can be used in methods to diagnose human aortic arch disease, such as coarctation, or atherosclerosis.

Levels of gridlock expression in a patient sample can be determined by using any of a number of standard techniques that are well known in the art. For example, gridlock expression in a biological sample (e.g., a blood or tissue sample, or amniotic fluid) from a patient can be monitored by standard northern blot analysis or by quantitative PCR (see, e.g., Ausubel et al., supra; *PCR Technology: Principles and Applications for DNA Amplification,* H. A. Ehrlich, Ed., Stockton Press, NY; Yap et al. *Nucl. Acids. Res.* 19:4294, 1991).

A biological sample obtained from a patient can be analyzed for one or more mutations in gridlock nucleic acid molecules using a mismatch detection approach. Generally, this approach involves PCR amplification of nucleic acid molecules from a patient sample, followed by identification of a mutation (i.e., a mismatch) by detection of altered hybridization, aberrant electrophoretic gel migration, binding, or cleavage mediated by mismatch binding proteins, or by direct nucleic acid molecule sequencing. Any of these techniques can be used to facilitate detection of mutant gridlock genes, and each is well known in the art. Examples of these techniques are described, for example, by Orita et al. (*Proc. Natl. Acad. Sci. U.S.A.* 86:2766–2770, 1989) and Sheffield et al. (*Proc. Natl. Acad. Sci. U.S.A.* 86:232–236, 1989).

Mismatch detection assays also provide an opportunity to diagnose a gridlock-mediated predisposition to a disease before the onset of symptoms. For example, a patient heterozygous for a gridlock mutation that suppresses normal gridlock biological activity or expression may show no clinical symptoms of a gridlock-related disease, and yet possess a higher than normal probability of developing a cardiovascular disease. Given such a diagnosis, patients can take precautions to minimize their exposure to adverse environmental factors and to carefully monitor their medical condition (for example, through frequent physical examinations). As mentioned above, this type of diagnostic approach can also be used to detect gridlock mutations in prenatal screens.

The gridlock diagnostic assays described above can be carried out using any biological sample (for example, a blood or tissue sample, or amniotic fluid) in which gridlock is normally expressed. Identification of a mutant gridlock gene can also be assayed using these sources for test samples. Alternatively, a gridlock mutation, particularly as part of a diagnosis for predisposition to a gridlock-associated disease, can be tested for using a DNA sample from any cell, for example, by mismatch detection techniques. Preferably, the DNA sample is subjected to PCR amplification prior to analysis.

In yet another diagnostic approach of the invention, an immunoassay is used to detect or monitor gridlock protein expression in a biological sample. gridlock-specific polyclonal or monoclonal antibodies (produced as described below) can be used in any standard immunoassay format (e.g., ELISA, Western blot, or RIA; see, e.g., Ausubel et al., supra) to measure gridlock polypeptide levels. These levels are compared to wild-type gridlock levels. For example, a decrease in gridlock production may be indicative of a condition or a predisposition to a condition involving insufficient gridlock biological activity, such as a cardiovascular disease.

Immunohistochemical techniques can also be utilized for gridlock detection. For example, a tissue sample can be obtained from a patient, sectioned, and stained for the presence of gridlock using an anti-gridlock antibody (see below) and any standard detection system (e.g., one that includes a secondary antibody conjugated to horseradish peroxidase). General guidance regarding such techniques can be found in, e.g., Bancroft et al., *Theory and Practice of Histological Techniques,* Churchill Livingstone, 1982, and Ausubel et al., supra.

In a preferred example, a combined diagnostic method can be employed that includes an evaluation of gridlock protein production (for example, by immunological techniques or the protein truncation test (Hogerrorst et al., *Nature Genetics* 10:208–212, 1995), and a nucleic acid molecule-based detection technique designed to identify more subtle gridlock mutations (for example, point mutations). As described above, a number of mismatch detection assays are available to those skilled in the art, and any preferred technique can be used. Mutations in gridlock can be detected that either result in loss of gridlock expression or loss of normal gridlock biological activity.

Therapeutic Methods Employing gridlock Nucleic Acid Molecules, Polypeptides and Antibodies The invention includes methods of treating or preventing gridlock-related diseases. As discussed above, a gridlock mutation may result in aortic arch disease, such as coarctation, early in development. Thus, the therapeutic methods of the invention may be, in some cases, targeted to prenatal treatment. For example, a fetus found to have a gridlock mutation can be administered a gene therapy vector including a normal gridlock gene or normal gridlock protein (see below). Such treatment may be required only for a short period of time, or may, in some form, be required throughout such a patient's lifetime. Any continued need for treatment, however, can be determined using, for example, the diagnostic methods described above. Also as discussed above, gridlock abnormalities may be associated with diseases in adults (e.g., aortic arch diseases and atherosclerosis), and thus adults can be subject to the therapeutic methods of the invention as well. These methods can also be used, for example, to promote blood vessel growth, which may be desirable, for example, in wound healing.

Therapies can be designed to circumvent or overcome a gridlock gene defect, or inadequate or excessive gridlock gene expression, and thus modulate and possibly alleviate conditions involving defects in gridlock genes or proteins. In considering various therapies, it is understood that such therapies are, preferably, targeted to the affected or potentially affected organs, for example, the aorta. Reagents that can be used to modulate gridlock biological activity can include, without limitation, full length gridlock polypeptides; gridlock DNA, mRNA, or antisense RNA; gridlock antibodies; and any compound that modulates gridlock biological activity, expression, or stability (see below).

Treatment or prevention of diseases resulting from a mutated gridlock gene can be accomplished, for example, by replacing a mutant gridlock gene with a normal gridlock gene, administering a normal gridlock gene, modulating the function of a mutant gridlock protein, delivering normal gridlock protein to the appropriate cells, or altering the levels of normal or mutant gridlock protein. It is also possible to correct a gridlock defect to modify the physiological pathway (e.g., a signal transduction pathway) in which the gridlock protein participates.

To replace a mutant protein with normal protein, or to add protein to cells that do not express sufficient or normal gridlock protein, it may be necessary to obtain large amounts of pure gridlock protein from cultured cell systems in which the protein is expressed (see, e.g., below). Delivery of the protein to the affected tissue can then be accomplished using appropriate packaging or administrating systems. Alternatively, small molecule analogs that act as gridlock agonists or antagonists can be administered to produce a desired physiological effect (see below).

Gene therapy is another therapeutic approach for preventing or ameliorating diseases caused by gridlock gene defects. Nucleic acid molecules encoding wild type gridlock can be delivered to cells that lack sufficient, normal gridlock biological activity (e.g., cells carrying mutations in gridlock genes). The nucleic acid molecules must be delivered to those cells in a form in which they can be taken up by the cells and so that sufficient levels of protein, to provide effective gridlock function, can be produced. Alternatively, for some gridlock mutations, it may be possible slow the progression of the resulting disease or to modulate gridlock activity by introducing another copy of a homologous gene bearing a second mutation in that gene, to alter the mutation, or to use another gene to block any negative effect.

Transducing retroviral, adenoviral, and adeno-associated viral vectors can be used for somatic cell gene therapy, especially because of their high efficiency of infection and stable integration and expression (see, e.g., Cayouette et al., *Human Gene Therapy* 8:423–430, 1997; Kido et al., *Current Eye Research* 15:833–844, 1996; Bloomer et al., *Journal of Virology* 71:6641–6649, 1997; Naldini et al., *Science* 272:263–267, 1996; and Miyoshi et al., *Proc. Natl. Acad. Sci., U.S.A.* 94:10319–1032, 1997). For example, the full length gridlock gene, or a portion thereof, can be cloned into a retroviral vector and expression can be driven from its endogenous promoter, from the retroviral long terminal repeat, or from a promoter specific for a target cell type of interest (such as aortic or other vascular cells). Other viral vectors that can be used include, for example, vaccinia virus, bovine papilloma virus, or a herpes virus, such as Epstein-Barr Virus (also see, for example, the vectors of Miller, *Human Gene Therapy* 15–14, 1990; Friedman, *Science* 244:1275–1281, 1989; Eglitis et al., *BioTechniques* 6:608–614, 1988; Tolstoshev et al., *Current Opinion in Biotechnology* 1:55–61, 1990; Sharp, *The Lancet* 337:1277–1278, 1991; Cornetta et al., *Nucleic Acid Research and Molecular Biology* 36:311–322, 1987; Anderson, *Science* 226:401–409, 1984; Moen, *Blood Cells* 17:407–416, 1991; Miller et al., *Biotechnology* 7:980–990, 1989; Le Gal La Salle et al., *Science* 259:988–990, 1993; and Johnson, *Chest* 107:77S-83S, 1995). Retroviral vectors are particularly well developed and have been used in clinical settings (Rosenberg et al., *N. Engl. J. Med* 323:370, 1990; Anderson et al, U.S. Pat. No. 5,399,346).

Gene transfer can also be achieved using non-viral means involving transfection in vitro. Such methods include use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal gridlock gene into a cultivatable cell type ex vivo, after which the cell (or its descendants) are injected into a targeted tissue.

Non-viral approaches can also be employed for the introduction of therapeutic DNA into cells predicted to be subject to diseases involving gridlock. For example, a gridlock nucleic acid molecule or an antisense nucleic acid molecule can be introduced into a cell by lipofection (Felgner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or, less preferably, micro-injection under surgical conditions (Wolff et al., *Science* 247:1465, 1990).

gridlock cDNA expression for use in gene therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct gridlock expression. The enhancers used can include, without limitation, those that are characterized as tissue- or cell-specific enhancers. Alternatively, if a gridlock genomic clone is used as a therapeutic construct (such clones can be identified by hybridization with gridlock cDNA, described above), regulation can be mediated by the cognate regulatory sequences, or, if desired, by regulatory sequences derived from a heterologous source, including any of the promoters or regulatory elements described above.

Antisense-based strategies can be employed to explore gridlock gene function and as a basis for therapeutic drug design. These strategies are based on the principle that sequence-specific suppression of gene expression (via transcription or translation) can be achieved by intracellular hybridization between genomic DNA or mRNA and a complementary antisense species. The formation of a hybrid RNA duplex interferes with transcription of the target gridlock-encoding genomic DNA molecule, or processing, transport, translation, or stability of the target gridlock mRNA molecule.

Antisense strategies can be delivered by a variety of approaches. For example, antisense oligonucleotides or antisense RNA can be directly administered (e.g., by intravenous injection) to a subject in a form that allows uptake into cells. Alternatively, viral or plasmid vectors that encode antisense RNA (or antisense RNA fragments) can be introduced into a cell in vivo or ex vivo. Antisense effects can be induced by control (sense) sequences; however, the extent of phenotypic changes are highly variable. Phenotypic effects induced by antisense effects are based on changes in criteria such as protein levels, protein activity measurement, and target mRNA levels.

For example, gridlock gene therapy can also be accomplished by direct administration of antisense gridlock mRNA to a cell that is expected to be adversely affected by the expression of wild-type or mutant gridlock. The antisense gridlock mRNA can be produced and isolated by any standard technique, but is most readily produced by in vitro transcription using an antisense gridlock cDNA under the control of a high efficiency promoter (e.g., the T7 promoter). Administration of antisense gridlock mRNA to cells can be carried out by any of the methods for direct nucleic acid molecule administration described above.

An alternative strategy for inhibiting gridlock function using gene therapy involves intracellular expression of an anti-gridlock antibody or a portion of an anti-gridlock antibody. For example, the gene (or gene fragment) encoding a monoclonal antibody that specifically binds to gridlock and inhibits its biological activity can be placed under the transcriptional control of a tissue-specific gene regulatory sequence.

The invention also includes the gridlock gene promoter and fragments thereof that direct gene expression in endothelial cells of arteries, such as the aorta. Such promoters can be used in the methods described above, to direct expression of gridlock, antisense gridlock RNA, or anti-gridlock antibodies or portions thereof, or can be used to express non-gridlock related molecules in arterial (e.g., aortic) endothelial cells.

Another therapeutic approach within the invention involves administration of recombinant gridlock polypeptide, either directly to the site of a potential or actual disease-affected tissue (for example, by injection) or systemically (for example, by any conventional recombinant protein administration technique). The dosage of gridlock depends on a number of factors, including the size and health of the individual patient, but, generally, between 0.1 mg and 100 mg, inclusive, are administered per day to an adult in any pharmaceutically acceptable formulation.

In a patient diagnosed as heterozygous for a gridlock mutation, or as susceptible to gridlock mutations or aberrant gridlock expression (even if those mutations or expression patterns do not yet result in alterations in gridlock expression or biological activity), any of the above-described therapies can be administered before the occurrence of the disease phenotype. In particular, compounds shown to modulate gridlock expression or gridlock biological activity can be administered to patients diagnosed with potential or actual diseases by any standard dosage and route of administration (see above). Alternatively, gene therapy using an antisense gridlock mRNA expression construct can be undertaken to reverse or prevent the gene defect prior to the development of the disease.

The methods of the present invention can be used to diagnose or treat the disorders described herein in any mammal, for example, humans, domestic pets, or livestock. Where a non-human mammal is treated or diagnosed, the gridlock polypeptide, nucleic acid molecule, or antibody employed is preferably specific for that species.

gridlock nucleic acid molecules and polypeptides can also be used in tissue engineering, for example, in the manufacture of artificial or partially artificial blood vessels. Coronary bypass surgery is, typically, carried out using vein grafts, which, as a consequence of the surgery, assume an arterial role. It is therefore desirable to impart arterial characteristics upon such vein grafts. As mentioned above, gridlock is an arterial marker and plays a role in arterial development and modeling. Thus, a vein graft can be treated with a gridlock nucleic acid molecule or polypeptide, as described above, to impart such characteristics on a vein graft. gridlock nucleic acid molecules and polypeptides can also be used in the construction of artificial blood vessels. For example, artificial matrices can be coated with smooth muscle cells on the outside and lined with endothelial cells. gridlock nucleic acid molecules or polypeptides can be used in association with any of these components to enhance the arterial nature of the artificial blood vessel.

Identification of Molecules that Modulate gridlock Biological Activity or Whose Biological Activity is Modulated by gridlock Isolation of the gridlock cDNA (as described herein) also facilitates the identification of molecules that increase or decrease gridlock biological activity. Similarly, molecules whose activity is modulated by gridlock biological activity can be identified. According to one approach, candidate molecules are added at varying concentrations to the culture medium of cells expressing gridlock mRNA. gridlock biological activity is then measured using standard techniques. The measurement of biological activity can include the measurement of gridlock protein and nucleic acid molecule levels, gridlock phosphorylation, or the effect of gridlock on vascular development.

If desired, the effect of candidate modulators on expression can, in the alternative, be measured at the level of gridlock protein production using the same general approach and standard immunological detection techniques, such as western blotting or immunoprecipitation with a gridlock-specific antibody (see below).

Candidate modulators can be purified (or substantially purified) molecules or can be one component of a mixture of compounds (e.g., an extract or supernatant obtained from cells; Ausubel et al., supra). In a mixed compound assay, gridlock expression is tested against progressively smaller subsets of the candidate compound pool (e.g., produced by standard purification techniques, e.g., HPLC or FPLC) until a single compound or minimal compound mixture is demonstrated to modulate gridlock expression.

Alternatively, or in addition, candidate compounds can be screened for those that modulate gridlock activity. In this approach, the level of aortic development and blood circulation in the presence of a candidate compound is compared to the level of aortic development and blood circulation in its absence, under equivalent conditions. Again, such a screen can begin with a pool of candidate compounds, from which one or more useful modulator compounds is isolated in a step-wise fashion.

Aortic development and blood circulation can be examined using, for example, the zebrafish system. The zebrafish, *Danio rerio,* is a convenient organism to use in genetic analysis of vascular development (see below). In addition to its short generation time and fecundity, it has an accessible and transparent embryo, allowing direct observation of blood vessel function from the earliest stages.

gridlock may also play a role in angiogenesis, which, as mentioned above, is the formation of blood vessels by sprouting and remodeling. Thus, compounds identified as modulating or mimicking gridlock or fragments thereof (e.g., gridlock fragments that include a YPPW motif), using the methods described above, can be used in methods for promoting (e.g., to promote wound healing) or inhibiting (e.g., to prevent tumor growth) angiogenesis.

The screening assays described above can be carried out in a variety of ways that are well known to those skilled in this art. These include using gridlock variants such as the gridlock$^{m145}$ mutant or by using fragments of gridlock.

A test compound that can be screened in the methods described above can be a chemical, be it naturally-occurring or artificially-derived. Such compounds can include, for example, polypeptides, synthesized organic molecules, naturally occurring organic molecules, nucleic acid molecules, and components thereof. Candidate gridlock modulators include peptide as well as non-peptide molecules (e.g., peptide or non-peptide molecules found, e.g., in a cell extract, mammalian serum, or growth medium in which mammalian cells have been cultured).

In general, novel drugs for prevention or treatment of gridlock-related diseases are identified from large libraries of both natural products, synthetic (or semi-synthetic) extracts, and chemical libraries using methods that are well known in the art. Those skilled in the field of drug discovery and development will understand that the precise source of test extracts or compounds is not critical to the screening methods of the invention. Accordingly, virtually any number of chemical extracts or compounds can be screened using these methods. Examples of such extracts or compounds include, but are not limited to, plant-, fungal-, prokaryotic-, or animal-based extracts, fermentation broths, and synthetic compounds, as well as modifications of existing compounds.

Numerous methods are also available for generating random or directed synthesis (e.g., semi-synthesis or total synthesis) of any number of chemical compounds, including, but not limited to, saccharide-, lipid-, peptide-, and nucleic acid molecule-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound can be readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their therapeutic activities for aortic arch or other cardiovascular (e.g., atherosclerosis) disorders can be employed whenever possible.

When a crude extract is found to regulate vascular development, further fractionation of the positive lead extract can be carried out to isolate chemical constituents responsible for the observed effect. Thus, the goal of the extraction, fractionation, and purification process is the careful characterization and identification of a chemical entity within the crude extract having a desired activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value can be subsequently analyzed using a mammalian vascular development model.

Administration of gridlock Polypeptides, gridlock Genes, and Modulators of gridlock Synthesis or Function A gridlock protein, gene, or modulator can be administered within a pharmaceutically-acceptable diluent, carrier, or excipient, in unit dosage form. Also, conventional pharmaceutical practice can be employed to provide suitable formulations or compositions in which to administer neutralizing gridlock antibodies or gridlock-inhibiting compounds (e.g., antisense gridlock or a gridlock dominant negative mutant) to patients suffering from a gridlock-related disease, such as an aortic arch disease or atherosclerosis. In addition, as noted above, gridlock may play a role in angiogenesis. Thus, gridlock polypeptides, genes, and modulators can be administered to stimulate or inhibit angiogenesis. For example, such a molecule may be administered to inhibit vein formation. Administration can begin before or after the patient is symptomatic.

Any appropriate route of administration can be employed, for example, administration can be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral. However, as noted above, preferably, the administration is local to the afflicted tissue, such as aortic or other cardiovascular tissue. Therapeutic formulations can be in the form of liquid solutions or suspensions; for oral administration, formulations can be in the form of tablets or capsules; and for intranasal formulations, in the form of powders, nasal drops, or aerosols.

Methods that are well known in the art for making formulations are found, for example, in *Remington's Pharmaceutical Sciences,* ($18^{th}$ edition), ed. A. Gennaro, 1990, Mack Publishing Company, Easton, Pa. Formulations for parenteral administration can, for example, contain excipients; sterile water; or saline; polyalkylene glycols, such as polyethylene glycol; oils of vegetable origin; or hydrogenated napthalenes. Biocompatible, biodegradable lactide polymer, lactide/glycolide copolymer, or polyoxyethylene-polyoxypropylene copolymers can be used to control the release of the compounds. Other potentially useful parenteral delivery systems for gridlock modulatory compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate, and deoxycholate, or can be oily solutions for administration in the form of nasal drops, or as a gel.

Synthesis of gridlock Proteins, Polypeptides, and Polypeptide Fragments

Those skilled in the art of molecular biology will understand that a wide variety of expression systems can be used to produce the recombinant gridlock proteins. As discussed further below, the precise host cell used is not critical to the invention. The gridlock proteins can be produced in a prokaryotic host (e.g., *E. coli*) or in a eukaryotic host (e.g., *S. cerevisiae,* insect cells such as Sf9 cells, or mammalian cells such as COS-1, NIH 3T3, or HeLa cells). These cells are commercially available from, for example, the American Type Culture Collection, Rockville, Md. (see also Ausubel et al., supra). The method of transformation and the choice of expression vehicle (e.g., expression vector) will depend on the host system selected. Transformation and transfection methods are described, e.g., in Ausubel et al., supra, and expression vehicles can be chosen from those provided, e.g. in Pouwels et al., supra. Specific examples of expression systems that can be used in the invention are described further, as follows.

The characteristics of cloned gridlock genes can be analyzed by introducing such genes into various cell types or using in vitro extracellular systems. The function of gridlock proteins produced in such cells or systems can then be examined under different physiological conditions. Alternatively, cell lines can be produced that over-express the gridlock gene product, allowing purification of gridlock for biochemical characterization, large-scale production, antibody production, and patient therapy.

For protein expression, eukaryotic or prokaryotic expression systems can be generated in which gridlock gene sequences are introduced into a plasmid or other vector, which is then used to transform living cells. Constructs in which full length gridlock cDNAs, containing the entire open reading frame, inserted in the correct orientation into an expression plasmid can be used for protein expression. Alternatively, portions of gridlock gene sequences, including wild type or mutant gridlock sequences, can be inserted. Prokaryotic and eukaryotic expression systems allow various important functional domains of gridlock proteins to be recovered, if desired, as fusion proteins, and then used for binding, structural, and functional studies, and also for the generation of antibodies.

Typical expression vectors contain promoters that direct synthesis of large amounts of mRNA corresponding to a nucleic acid molecule that has been inserted into the vector. They can also include a eukaryotic or prokaryotic origin of replication, allowing for autonomous replication within a host cell, sequences that confer resistance to an otherwise toxic drug, thus allowing vector-containing cells to be selected in the presence of the drug, and sequences that increase the efficiency with which the synthesized mRNA is translated. Stable long-term vectors can be maintained as freely replicating entities by using regulatory elements of, for example, viruses (e.g., the OriP sequences from the Epstein Barr Virus genome). Cell lines can also be produced that have the vector integrated into genomic DNA of the cells, and, in this manner, the gene product can be produced in the cells on a continuous basis.

Expression of foreign molecules in bacteria, such as *Escherichia coli,* requires the insertion of a foreign nucleic acid molecule, e.g., a gridlock nucleic acid molecule, into a bacterial expression vector. Such plasmid vectors include several elements required for the propagation of the plasmid in bacteria, and for expression of foreign DNA contained within the plasmid. Propagation of only plasmid-bearing bacteria is achieved by introducing, into the plasmid, a selectable marker-encoding gene that allows plasmid-bearing bacteria to grow in the presence of an otherwise toxic drug. The plasmid also contains a transcriptional promoter capable of directing synthesis of large amounts of mRNA from the foreign DNA. Such promoters can be, but are not necessarily, inducible promoters that initiate transcription upon induction by culture under appropriate conditions (e.g., in the presence of a drug that activates the promoter). The plasmid also, preferably, contains a polylinker to simplify insertion of the gene in the correct orientation within the vector.

Once an appropriate expression vector containing a gridlock gene, or a fragment, fusion, or mutant thereof, is constructed, it can be introduced into an appropriate host cell using a transformation technique, such as, for example, calcium phosphate transfection, DEAE-dextran transfection, electroporation, microinjection, protoplast fusion, or liposome-mediated transfection. Host cells that can be transfected with the vectors of this invention can include, but are not limited to, E. coli or other bacteria, yeast, fungi, insect cells (using, for example, baculoviral vectors for expression), or cells derived from mice, humans, or other animals. Mammalian cells can also be used to express gridlock proteins using a virus expression system (e.g., a vaccinia virus expression system) described, for example, in Ausubel et al., supra.

In vitro expression of gridlock proteins, fusions, polypeptide fragments, or mutants encoded by cloned DNA can also be carried out using the T7 late-promoter expression system. This system depends on the regulated expression of T7 RNA polymerase, an enzyme encoded in the DNA of bacteriophage T7. The T7 RNA polymerase initiates transcription at a specific 23-bp promoter sequence called the T7 late promoter. Copies of the T7 late promoter are located at several sites on the T7 genome, but none is present in E. coli chromosomal DNA. As a result, in T7-infected E. coli, T7 RNA polymerase catalyzes transcription of viral genes, but not E. coli genes. In this expression system, recombinant E. coli cells are first engineered to carry the gene encoding T7 RNA polymerase next to the lac promoter. In the presence of IPTG, these cells transcribe the T7 polymerase gene at a high rate and synthesize abundant amounts of T7 RNA polymerase. These cells are then transformed with plasmid vectors that carry a copy of the T7 late promoter protein. When IPTG is added to the culture medium containing these transformed E. coli cells, large amounts of T7 RNA polymerase are produced. The polymerase then binds to the T7 late promoter on the plasmid expression vectors, catalyzing transcription of the inserted cDNA at a high rate. Since each E. coli cell contains many copies of the expression vector, large amounts of mRNA corresponding to the cloned cDNA can be produced in this system and the resulting protein can be radioactively labeled.

Plasmid vectors containing late promoters and the corresponding RNA polymerases from related bacteriophages, such as T3, T5, and SP6, can also be used for in vitro production of proteins from cloned DNA. E. coli can also be used for expression using an M13 phage, such as mGPI-2. Furthermore, vectors that contain phage lambda regulatory sequences, or vectors that direct the expression of fusion proteins, for example, a maltose-binding protein fusion protein or a glutathione-S-transferase fusion protein, also can be used for expression in E. coli.

Eukaryotic expression systems are useful for obtaining appropriate post-translational modification of expressed proteins. Transient transfection of a eukaryotic expression plasmid containing a gridlock gene, into a eukaryotic host cell allows the transient production of gridlock by the transfected host cell. gridlock proteins can also be produced by a stably-transfected eukaryotic (e.g., mammalian) cell line. A number of vectors suitable for stable transfection of mammalian cells are available to the public (see, e.g., Pouwels et al., *Cloning Vectors: A Laboratory Manual,* 1985, Supp. 1987), as are methods for constructing lines including such cells (see, e.g., Ausubel et al., supra).

In one example, cDNA encoding a gridlock protein, fusion, mutant, or polypeptide fragment is cloned into an expression vector that includes the dihydrofolate reductase (DHFR) gene. Integration of the plasmid and, therefore, integration of the gridlock-encoding gene, into the host cell chromosome is selected for by inclusion of 0.01–300 $\mu$M methotrexate in the cell culture medium (Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al., supra. These methods generally involve extended culture in medium containing gradually increasing levels of methotrexate. The most commonly used DHFR-containing expression vectors are pCVSEII-DHFR and pAdD26SV(A) (described, for example, in Ausubel et al., supra). The host cells described above or, preferably, a DHFR-deficient CHO cell line (e.g., CHO DHFR⁻ cells, ATCC Accession No. CRL 9096) are among those that are most preferred for DHFR selection of a stably-transfected cell line or DHFR-mediated gene amplification.

Another preferred eukaryotic expression system is the baculovirus system using, for example, the vector pBacPAK9, which is available from Clontech (Palo Alto, Calif.). If desired, this system can be used in conjunction with other protein expression techniques, for example, the myc tag approach described by Evan et al. (*Molecular and Cellular Biology* 5:3610–3616, 1985).

Once a recombinant protein is expressed, it can be isolated from the expressing cells by cell lysis followed by protein purification techniques, such as affinity chromatography. In this example, an anti-gridlock antibody, which can be produced by the methods described herein, can be attached to a column and used to isolate the recombinant gridlock proteins. Lysis and fractionation of gridlock protein-harboring cells prior to affinity chromatography can be performed by standard methods (see e.g., Ausubel et al., supra). Once isolated, the recombinant protein can, if desired, be purified further by e.g., by high performance liquid chromatography (HPLC; e.g., see Fisher, *Laboratory Techniques In Biochemistry and Molecular Biology,* Work and Burdon, Eds., Elsevier, 1980).

Polypeptides of the invention, particularly short gridlock fragments and longer fragments of the N-terminus and C-terminus of the gridlock protein, can also be produced by chemical synthesis (e.g., by the methods described in *Solid Phase Peptide Synthesis,* 2$^{nd}$ ed., 1984, The Pierce Chemical Co., Rockford, Ill.). These general techniques of polypeptide expression and purification can also be used to produce and isolate useful gridlock polypeptide fragments or analogs, as described herein.

As discussed above, eukaryotic cells expressing gridlock proteins can be used to identify and test the effectiveness of pharmacological agents on gridlock-associated diseases. Such cells can also be used to produce gridlock polypeptides for use in the methods described above. Eukaryotic cell expression of gridlock proteins facilitates further studies of the gridlock gene and gene products, including determination of proper expression and post-translational modifications required for biological activity, and identifying regulatory elements located in the 5', 3', and intron regions of gridlock genes and determining their roles in tissue regulation of gridlock protein expression. It also permits the production of large amounts of normal and mutant proteins for isolation and purification, and the use of cells expressing gridlock proteins as a functional assay system for antibodies generated against the protein. Expression of gridlock proteins, fusions, mutants, and polypeptide fragments in eukaryotic cells also enables the study of the function of the normal complete protein, specific portions of the protein, or of naturally occurring polymorphisms and artificially-produced mutated proteins. The gridlock DNA sequences can be altered using procedures known in the art, such as restriction endonuclease digestion, DNA polymerase fill-in, exonuclease deletion, terminal deoxynucleotide transferase extension, ligation of synthetic or cloned DNA sequences, and site-directed sequence alteration using specific oligonucleotides and PCR.

gridlock Fragments

Polypeptide fragments that include various portions of gridlock proteins are useful in identifying the domains of gridlock important for its biological activities, such as protein-protein interactions and transcription. Methods for generating such fragments are well known in the art (see, for example, Ausubel et al., supra), using the nucleotide sequences provided herein. For example, a gridlock protein fragment can be generated by PCR amplifying a desired gridlock nucleic acid molecule fragment using oligonucleotide primers designed based upon the gridlock nucleic acid sequences. Preferably, the oligonucleotide primers include unique restriction enzyme sites that facilitate insertion of the amplified fragment into the cloning site of an expression vector (e.g., a mammalian expression vecoor, see above). This vector can then be introduced into a cell (e.g., a mammalian cell; see above) by artifice, using any of the various techniques known in the art such as those described herein, resulting in the production of a gridlock polypeptide fragment in the cell containing the expression vector.

gridlock polypeptide fragments (e.g., chimeric fusion proteins) can also be used to raise antibodies specific for various regions of gridlock using, for example, the methods described below. Preferred gridlock fragments include, without limitation, fragments corresponding to the C-terminal domain containing the YRPW motif, fragments lying outside the conserved regions, and fragments thereof.

gridlock Antibodies

To prepare polyclonal antibodies, gridlock proteins, fragments of gridlock proteins, or fusion proteins containing defined portions of gridlock proteins can be synthesized in, e.g., bacteria by expression of corresponding DNA sequences contained in a suitable cloning vehicle. Fusion proteins are commonly used as a source of antigen for producing antibodies. Two widely used expression systems for E. coli are lacZ fusions using the pUR series of vectors and trpE fusions using the pATH vectors. The proteins can be purified, and then coupled to a carrier protein, mixed with Freund's adjuvant (to enhance stimulation of the antigenic response in an inoculated animal), and injected into rabbits or other laboratory animals. Alternatively, protein can be isolated from gridlock-expressing cultured cells. Following booster injections at bi-weekly intervals, the rabbits or other laboratory animals are then bled and the sera isolated. The sera can be used directly or can be purified prior to use by various methods, including affinity chromatography employing reagents such as Protein A-Sepharose, antigen-Sepharose, and anti-mouse-Ig-Sepharose. The sera can then be used to probe protein extracts from gridlock-expressing tissue fractionated by polyacrylamide gel electrophoresis to identify gridlock proteins. Alternatively, synthetic peptides can be made that correspond to antigenic portions of the protein and used to inoculate the animals.

To generate peptide or full-length protein for use in making, for example, gridlock-specific antibodies, a gridlock coding sequence can be expressed as a C-terminal or N-terminal fusion with glutathione S-transferase (GST; Smith et al., Gene 67:31–40, 1988). The fusion protein can be purified on glutathione-Sepharose beads, eluted with glutathione, cleaved with a protease, such as thrombin or Factor-Xa (at the engineered cleavage site), and purified to the degree required to successfully immunize rabbits. Primary immunizations can be carried out with Freund's complete adjuvant and subsequent immunizations performed with Freund's incomplete adjuvant. Antibody titers can be monitored by Western blot and immunoprecipitation analyses using the protease-cleaved gridlock fragment of the GST-gridlock fusion protein. Immune sera can be affinity purified using CNBr-Sepharose-coupled gridlock protein. Antiserum specificity can be determined using a panel of unrelated GST fusion proteins.

Alternatively, monoclonal gridlock antibodies can be produced by using, as an antigen, gridlock protein isolated from gridlock-expressing cultured cells or gridlock protein isolated from tissues. The cell extracts, or recombinant protein extracts containing gridlock protein, can, for example, be injected with Freund's adjuvant into mice. Several days after being injected, the mouse spleens can be removed, the tissues disaggregated, and the spleen cells suspended in phosphate buffered saline (PBS). The spleen cells serve as a source of lymphocytes, some of which would be producing antibody of the appropriate specificity. These can then be fused with permanently growing myeloma partner cells, and the products of the fusion plated into a number of tissue culture wells in the presence of selective agents, such as hypoxanthine, aminopterine, and thymidine (HAT). The wells can then be screened by ELISA to identify those containing cells making antibody capable of binding to a gridlock protein, polypeptide fragment, or mutant thereof. These cells can then be re-plated and, after a period of growth, the wells containing these cells can be screened again to identify antibody-producing cells. Several cloning procedures can be carried out until over 90% of the wells contain single clones that are positive for specific antibody production. From this procedure, a stable line of clones that produce the antibody can be established. The monoclonal antibody can then be purified by affinity chromatography using Protein A Sepharose and ion-exchange chromatography, as well as variations and combinations of these techniques. Once produced, monoclonal antibodies are also tested for specific gridlock protein recognition by Western blot or immunoprecipitation analysis (see, e.g., Kohler et al., Nature 256:495, 1975; Kohler et al., European Journal of Immunology 6:511, 1976; Kohler et al., European Journal of Immunology 6:292, 1976; Hammerling et al., In Monoclonal Antibodies and T Cell Hybridomas, Elsevier, New York, N.Y., 1981; Ausubel et al., supra).

As an alternate or adjunct immunogen to GST fusion proteins, peptides corresponding to relatively unique hydrophilic regions of gridlock can be generated and coupled to keyhole limpet hemocyanin (KLH) through an introduced C-terminal lysine. Antiserum to each of these peptides can be similarly affinity-purified on peptides conjugated to BSA, and specificity tested by ELISA and Western blotting using peptide conjugates, and by Western blotting and immunoprecipitation using gridlock, for example, expressed as a GST fusion protein.

Antibodies of the invention can be produced using gridlock amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson et al., *CABIOS* 4:181, 1988. These fragments can be generated by standard techniques, e.g., by the PCR, and cloned into the pGEX expression vector. GST fusion proteins can be expressed in *E. coli* and purified using a glutathione-agarose affinity matrix (Ausubel et al., supra). To generate rabbit polyclonal antibodies, and to minimize the potential for obtaining antisera that is non-specific, or exhibits low-affinity binding to a gridlock, two or three fusions are generated for each protein, and each fusion is injected into at least two rabbits. Antisera are raised by injections in series, preferably including at least three booster injections.

In addition to intact monoclonal and polyclonal anti-gridlock antibodies, the invention features various genetically engineered antibodies, humanized antibodies, and antibody fragments, including F(ab')2, Fab', Fab, Fv, and sFv fragments. Truncated versions of monoclonal antibodies, for example, can be produced by recombinant methods in which plasmids are generated that express the desired monoclonal antibody fragment(s) in a suitable host. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also included in the invention (Green et al., *Nature Genetics* 7:13–21, 1994).

Ladner (U.S. Pat. Nos. 4,946,778 and 4,704,692) describes methods for preparing single polypeptide chain antibodies. Ward et al., *Nature* 341:544–546, 1989, describes the preparation of heavy chain variable domains, which they term "single domain antibodies," and which have high antigen-binding affinities. McCafferty et al., *Nature* 348:552–554, 1990, show that complete antibody V domains can be displayed on the surface of fd bacteriophage, that the phage bind specifically to antigen, and that rare phage (one in a million) can be isolated after affinity chromatography. Boss et al., U.S. Pat. No. 4,816,397, describes various methods for producing immunoglobulins, and immunologically functional fragments thereof, that include at least the variable domains of the heavy and light chains in a single host cell. Cabilly et al., U.S. Pat. No. 4,816,567, describes methods for preparing chimeric antibodies.

Use of gridlock Antibodies

Antibodies to gridlock proteins can be used, as noted above, to detect gridlock proteins or to inhibit the biological activities of gridlock proteins. For example, a nucleic acid molecule encoding an antibody or portion of an antibody can be expressed within a cell to inhibit gridlock function. In addition, the antibodies can be coupled to compounds, such as radionuclides and liposomes for diagnostic or therapeutic uses. Antibodies that specifically recognize extracellular domains of gridlock are useful for targeting such attached moieties to cells displaying such gridlock polypeptide domains at their surfaces. Antibodies that inhibit the activity of a gridlock polypeptide described herein can also be useful in preventing or slowing the development of a disease caused by inappropriate expression of a wild type or mutant gridlock gene.

Detection Of gridlock Gene Expression

As noted, the antibodies described above can be used to monitor gridlock protein expression. In situ hybridization of RNA can be used to detect the expression of gridlock genes. RNA in situ hybridization techniques rely upon the hybridization of a specifically labeled nucleic acid probe to the cellular RNA in individual cells or tissues. Therefore, RNA in situ hybridization is a powerful approach for studying tissue- and temporal-specific gene expression. In this method, oligonucleotides, cloned DNA fragments, or antisense RNA transcripts of cloned DNA fragments corresponding to unique portions of gridlock genes are used to detect specific mRNA species, e.g., in the tissues of animals, such as mice, at various developmental stages. Other gene expression detection techniques are known to those of skill in the art and can be employed for detection of gridlock gene expression.

Identification of Additional gridlock Genes

Standard techniques, such as the polymerase chain reaction (PCR) and DNA hybridization, can be used to clone gridlock homologues in other species and gridlock-related genes in humans. gridlock-related genes and homologues can be readily identified using low-stringency DNA hybridization or low-stringency PCR with human gridlock probes or primers. Degenerate primers encoding human gridlock or human gridlock-related amino acid sequences can be used to clone additional gridlock-related genes and homologues by RT-PCR.

Construction of Transgenic Animals and Knockout Animals

Characterization of gridlock genes provides information that allows gridlock knockout animal models to be developed by homologous recombination. Preferably, a gridlock knockout animal is a mammal, most preferably a mouse. Similarly, animal models of gridlock overproduction can be generated by integrating one or more gridlock sequences into the genome of an animal, according to standard transgenic techniques. Moreover, the effect of gridlock gene mutations (e.g., dominant gene mutations) can be studied using transgenic mice carrying mutated gridlock transgenes or by introducing such mutations into the endogenous gridlock gene, using standard homologous recombination techniques.

A replacement-type targeting vector, which can be used to create a knockout model, can be constructed using an isogenic genomic clone, for example, from a mouse strain such as 129/Sv (Stratagene Inc., LaJolla, Calif.). The targeting vector can be introduced into a suitably-derived line of embryonic stem (ES) cells by electroporation to generate ES cell lines that carry a profoundly truncated form of a gridlock gene. To generate chimeric founder mice, the targeted cell lines are injected into a mouse blastula-stage embryo. Heterozygous offspring can be interbred to homozygosity. gridlock knockout mice provide a tool for studying the role of gridlock in embryonic development and in disease. Moreover, such mice provide the means, in vivo, for testing therapeutic compounds for amelioration of diseases or conditions involving a gridlock-dependent or gridlock-affected pathway.

Experimental Results

The grl gene was isolated using positional cloning strategies. grl encodes a novel basic helix-loop-helix (bHLH)

protein, with a carboxyl-terminal motif characteristic of the hairy-related family of bHLH proteins. These bHLH proteins have been shown to be important for cell fate determination in other cell types. In the Drosophila nervous system, for example, members of the hairy family act as transcriptional repressors that help to pattern and establish "equivalence groups" of neuronal progenitor cells. It is likely that grl plays a similar role in angioblasts, functioning as an artery-specific marker. It is also possible that grl functions at the VEGF/FLK pathway, which appears to be critical for vasculogenesis (Fouquet et al., *Developmental Biology* 183:37–48, 1997; Liao et al., Development 124:381–389, 1997).

The grl$^{m145}$ mutant was found to have a mutation in the stop codon following the carboxyl-terminal motif characteristic of the hairy-related family of bHLH proteins. This mutation can be complemented by the injection of a wild type grl mRNA, but not by a grl mRNA lacking the carboxyl-terminal motif.

grl was expressed in the lateral plate mesoderm at the early stage of the embryos, anticipating vessel formation, and thereafter was selectively expressed in the aorta. The grl mutation clearly marks cells of the nascent aorta, even prior to formation of a lumen or onset of blood flow, and is not expressed by the vein, suggesting that angioblasts can be distinctive even prior to assembly. This mutation perturbs assembly of the aorta, but does not affect the axial veins or the vessels of the head. Thus, grl establishes an aorta-specific endothelial cell fate.

As indicated above, the aorta is a region affected by several congenital disorders, some of which perturb a region analogous, on an embryological basis, to the anterior aortic bifurcation, the region most affected by the grl mutation. Some of these disorders, such as coarctation, show a high sibling recurrence, suggesting a genetic basis.

Positional Cloning of the grl Gene

Figure 1:
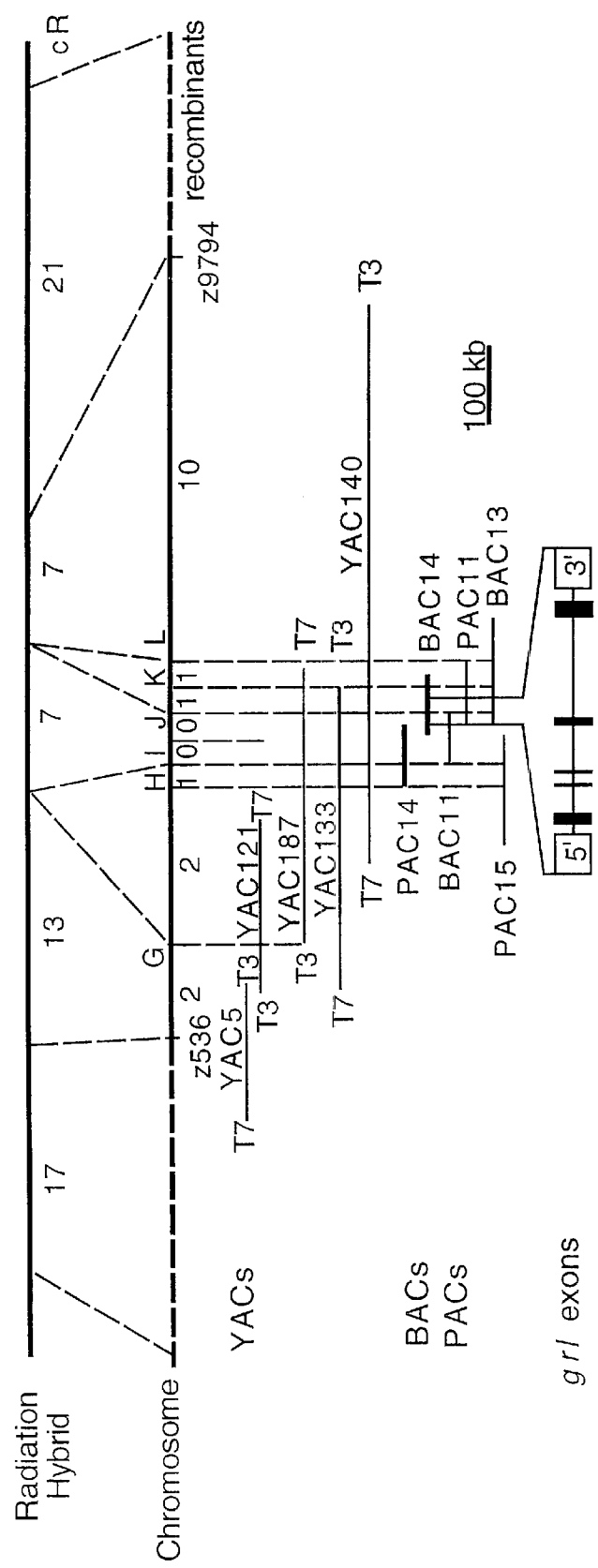
FIG. 1 is a diagram showing the local genetic, physical, and radiation hybrid map of the zebrafish gridlock region.

To clone the grl mutation, its position was first established on a zebrafish genetic map, using single strand length polymorphism (SSLP) markers and random amplified polymorphic DNA (RAPD) molecules, and then a physical map of the region was generated using yeast artificial chromosomes (YACs) and bacterial artificial chromosomes (BACs) (FIG. 1; G, H, I, J, K, and L correspond to YAC, BAC, and PAC ends). Some of the polymorphic landing markers were used to integrate the local radiation hybrid (RH) map, genetic map, and physical map at the mutation region, indicating that these markers are correlated at their corresponding positions (FIG. 1). The number of recombinants between the markers and the gridlock locus are shown below the chromosome line. Some of the genetic markers were used for genotyping on the RH panel, and the distance (cM) between these markers is indicated below the RH line.

The gridlock m145 allele was mapped to linkage group 20 between genetic markers z536 and z9794, with 1,200 mutants providing 2,400 informative meioses. Marker z536 was used for chromosomal walking, and was isolated to link to the gridlock locus by bulk segregation analysis. Five and twelve recombinants, among the 1,200 mutants, were identified using markers z536 and z9794, respectively. Recombinant analysis defined a 0.71 cM interval containing the mutation.

A YAC map of about 2 megabases (Mb), spanning the region containing the gridlock mutation, was then constructed. The YAC contig was constructed from YAC5, YAC121, YAC133, YAC187, and YAC140, and the YAC ends were rescued by self-circularization (Zhong et al., *Genomics* 48:136–138, 1998) and sequenced. The YAC sizes, from 300 Kb to 1.2 Mb, were determined by pulsed field gel electrophoresis. Recombinant fine mapping analysis was performed using single stranded conformation polymorphisms (SSCP) from the rescued YAC end sequences. Polymorphisms were detected by SSCP analysis from the T3 ends of both YAC187 and YAC133, and identified one recombinant after the mutation, and three recombinants before the mutation, respectively. These experiments physically located grl$^{m145}$ between the T3 ends of YAC 133 and YAC 187, in a 500 Kb interval.

To refine this 500 Kb interval further, a BAC/PAC contig from three BACs and three PACs, using the T3 end of YAC133 as a starting point, was assembled. SSCP analyses, from the end sequences of PAC14, BAC11, and PAC11 identified 1 recombinant before the mutation, two 0 recombinants at the locus, and 2 recombinants after the mutation, corresponding to the recombination points zP14, zB11a, zB11b, and zP11. Thus, fine mapping, using recombination frequency among 2,400 meioses, permitted the refinement of the 500 Kb interval to 120 Kb enclosed on overlapping BAC14 and PAC14 (FIG. 1). Recombinant fine mapping analysis was performed using single stranded conformation polymorphisms (SSCP) from the sequence of rescued BAC and PAC ends. The BAC/PAC ends were rescued by inverse PCR or directly sequenced.

To identify the grl gene, five-fold shotgun sequencing from genomic libraries, constructed from BAC14 and PAC14 containing the grl mutation, was performed. Ten-fold shotgun libraries of BAC14 and PAC14 were made from sheared DNA using Sonic Dismembrator (8×12"), followed by Mung Bean Nuclease treatment, two sizing selections on an agarose gel, and blunt-end ligation. High throughput minipreps were performed using Qiagene Robot 9600, and shotgun sequencing, estimated to provide five-fold coverage, was carried out using an ABI 377 sequencer. Large contigs were assembled using 2,000 shotgun sequences. The flanking sequence of the vector was clipped off using CrossMatch. The sequences of both BAC14 and PAC14 were analyzed by the phred/phrap/consed program, establishing 11 sequence contigs. The sequence contigs were assembled using Phrap, and edited by Consed. Computational algorithms (combinatory Genescan and Blast Search) identified exons, introns, and exon-intron boundaries that formed four putative genes at the grl region (termed genes A to D).

The BAC and PAC were then used as probes to screen embryonic cDNA libraries. cDNAs were isolated from whole mount in situ hybridization and histology analyses. A 24 hour-cDNA library was screened with $\alpha^{32}$P-labeled BAC14 or PAC14, which was pre-annealed overnight in a genomic repeat-repressing cocktail (5×SSC, 2.5 μg/μl genomic DNA, 0.5 μg/μl CA and GT oligo, 0.5 μg/μl of mermaid and epd repeats) in hybridization buffer (6×SSC, 0.5% SDS, 100 μg/μl calf thymus DNA). The filters were washed in 2×SSC/0.1% SDS, 0.2×SSC/0.1%SDS. Subsequent fine mapping with single nucleotide polymorphism (SNPs) showed gene B to be outside of the grl region. The other three genes were sequenced from wild type and mutant embryos, and their expression patterns examined. Gene C appeared to be a zebrafish ortholog of human Pex7, and Gene D appeared to be novel. No consistent mutations were found in the coding regions of C and D in mutant embryos, and the expression pattern of C and D was not related to the aorta or surrounding tissues.

Gene A was expressed at the merging regions of bilateral dorsal aortae. As the grl mutant was defective in the merging process from bilateral dorsal aortae to single midline dorsal aorta, gene A seemed a promising candidate. Genomic sequence analysis defined six coding exons and intron-exon boundaries of gene A. To search for a mutation, all exons and intron-exon boundaries of gene A in grl$^{m145}$ mutants and homologous wild type siblings were sequenced. A single T to A transversion mutation, also found from sequencing grl mutant cDNA isolated by RT-PCR, was identified.

Gene A, thus, mapped to the critical interval (FIG. 1) and had a mutation present in grl$^{m145}$ mutant embryos, but absent in wild type siblings. Furthermore, as shown below, Gene A was expressed selectively in the aorta at the merging regions of bilateral dorsal aortae, consistent with the grl phenotype, and its microinjected synthetic wild type RNA rescued the grl mutant. Therefore, gene A is the grl gene.

The Protein Encoded by grl

Translation of the grl genomic DNA and cDNA sequences predicted that the zebrafish grl encoded a novel protein of 301 amino acids (FIG. 2A; SEQ ID NO:2). The human ortholog of grl, referred to as hgrl (FIG. 2A; SEQ ID NO:4) was also identified by EST database searching, and was assembled from human ESTs A1727779 and AA116067. Alignment of the predicted human and zebrafish amino acid sequences of the grls indicated 78% overall identity, with more extensive identity in the bHLH (100%) and Orange (95%) domains. Outside these domains, the grl proteins are 65% identical. The grl proteins have a YRPW protein interaction domain motif at the carboxyl terminal.

Figure 2D:
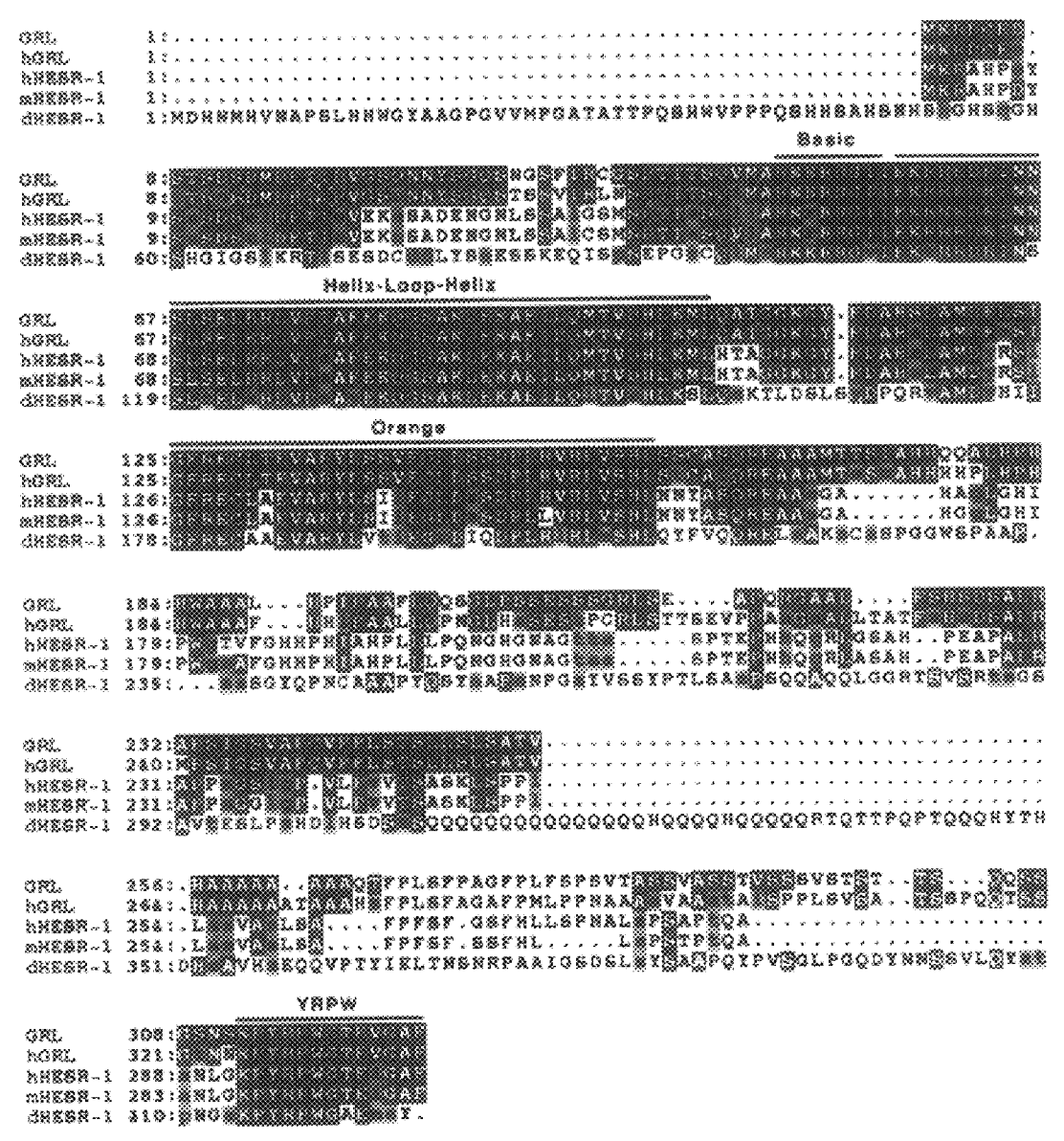

The grl genes show sequence similarity to the hairy/enhancer of split-related (hesr) bHLH genes (Fisher et al., *Molecular and Cellular Biology*, 2670–2677, 1996; Kokubo et al., *Biochemical Biophysical Research Communications* 260:459–465, 1999). hesr genes (FIGS. 2B and 2D) are a subgroup of the hairy-related bHLH genes. Like other hairy genes, they are predicted to have an N-terminal bHLH domain, an Orange domain, and a protein-protein interaction motif near the carboxyl terminus. FIG. 2B shows a sequence comparison of the grl genes with the hesr genes in the bHLH domain, Orange domain, and C-terminal motif. In particular, there are six amino acids that are distinct between grl and hesr proteins in the Orange domain. The sequence alignment was performed using Pileup of GCG package (Version 10) and displayed by interface of MacBoxshade 2.15. The grl genes are related to the mouse Hey2/HRT-2 gene, which is also a member of the hesr gene family of bHLH genes (Leimeister et al., Mechanisms of Development 85:173–177, 1999).

The carboxyl-terminal motif is critical for action of the hairy proteins, but is divergent in hesr proteins. The hesr proteins are distinguished from other members of the hairy-related family by a glycine-for-proline substitution in the basic domain, and a change from the carboxyl-terminal WRPW motif to YRPW, the latter being embedded within a 13 amino acid hesr motif. grl shows the highest similarity to the hesr, hes, and hairy proteins in the bHLH domain (85%), some similarity in the Orange domain (55%), and also has a YRPW motif, a protein-protein interaction domain, at its carboxyl terminal. grl proteins show only about 21% identity with hesr proteins outside the conserved regions. The low extent of overall similarity between these proteins (25%–43%) indicates that they belong to distinct gene families.

The genomic sequence of grl mutant embryos revealed a consistent T-to-A transversion mutation, when compared with wild type, that changed an invariant stop codon to glycine and added an extra 44 amino acids to the wild type protein (FIG. 2C). The mutation was found in the genomic region of all eight grl mutant embryos examined and also found in RT-PCR of cDNA from a pool of 10 mutant embryos. The position of the mutation at the carboxyl terminus, adjacent to the YRPW domain, suggested a role in protein-protein interaction, although protein stability can be affected as well.

Expression of grl mRNA

Figure 3A:
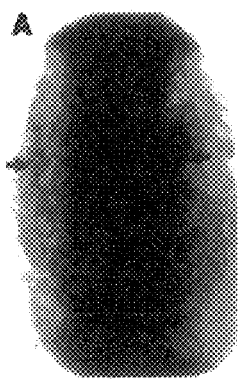
FIG. 3A is a histological section showing expression of grl mRNA as bilateral stripes (arrows) at the 10 somite stage (dorsal view).
Figure 3E:
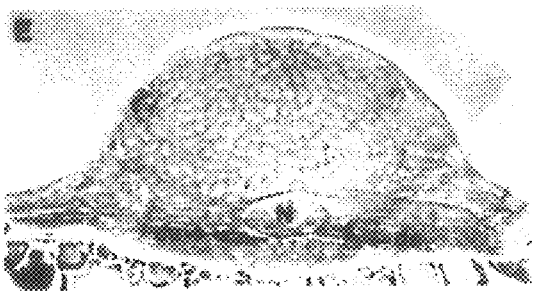
FIG. 3E is a transverse histological section of the anterior trunk showing grl expression at the paired dorsal aortae (arrows) ventral to the notochord, but not at the bilateral cardinal veins (arrowheads).
Figure 3B:
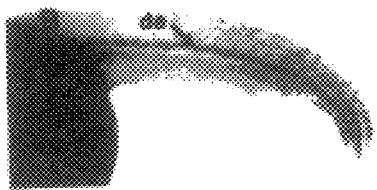
FIGS. 3B–C are histological sections showing the lateral view of the anterior trunk, posterior trunk, and tail, showing the grl transcripts at the dorsal aorta (arrows).
Figure 3J:
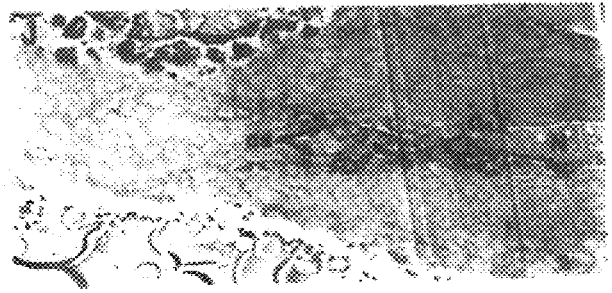
FIG. 3J is a longitudinal histological section of the anterior trunk showing the dorsal view of selective expression of the grl at the aortic bifurcation at the 25 somite stage (arrows).
Figure 3C:
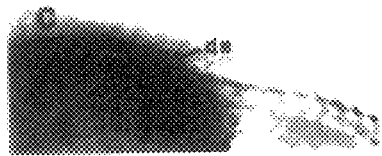

To examine patterns of grl expression during zebrafish embryogenesis, whole mount in situ RNA hybridization was carried out at various time points. The grl transcript was first detected at the 10 somite stage, prior to vessel formation, in the anterior and posterior regions of the lateral plate mesoderm, and appeared as bilateral stripes (FIG. 3A, dorsal view).

Whole amount RNA in situ hybridization was carried out as described (Jowett et al., *Trends Genet.* 10:73–74, 1994). A 1891-bp fragment of cDNA that contains both ORF and 3'UTR was subcloned for in vitro transcription. For histological analysis, specimens were fixed in 4% paraformaldehyde, dehydrated, and embedded in plastic (JB-4). Nomarski photomicroscopy was performed with an Axiophot using Ektachrome 160T film (Zeiss). Wild M5 and M10 dissecting microscopes, equipped with Nikon cameras, were used for low-power photomicroscopy. Embryos were staged according to Kimmel et al. (*Dev. Dyn.* 203:253–310, 1995).

Figure 3D:
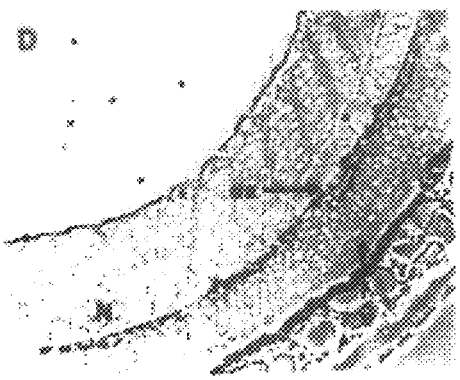
FIG. 3D is a sagittal histological sections of the posterior trunk showing the lumen of the dorsal aorta with the grl expression (arrow) and the grl-negative cells at axial veins (arrow).
Figure 3F:
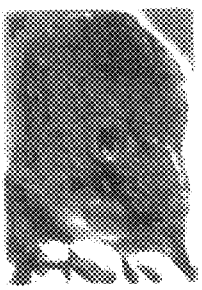
FIGS. 3F–G are transverse histological sections of posterior trunk showing grl expression in the endothelial cells at the middleline dorsal aorta beneath the notochord (arrowhead), and extending into what is likely a sprout (the intersomitic artery; small arrow), but not in the vein (arrows).
Figure 3G:
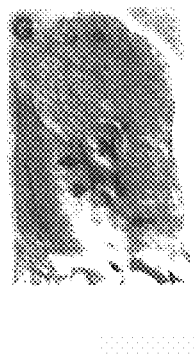
Figure 3H:
FIG. 3H is a transverse histological section of posterior trunk showing fli expression at both the middleline dorsal aorta (arrowhead) and the axial vein (arrows).
Figure 3I:
FIG. 3I is a transverse histological section through the anterior trunk at the level of the first somite; fli is expressed at bilateral common cardinal veins (arrowheads) and the paired dorsal aortae (arrows).

By the 14-somite stage, the grl-expressing cells began to converge towards the ventral midline to form the primordium of the dorsal aorta, just ventral to the notochord. No grl-expressing cells were observed in the region of the precursors of the axial vein, below the aorta. At the 30-somite stage, grl was expressed strongly throughout the dorsal aorta (FIGS. 3B–3C, lateral view of the anterior trunk, posterior trunk, and tail showing the grl transcripts at the dorsal aorta; FIG. 3D, sagittal histological sections of the posterior trunk showing the lumen of the dorsal aorta with grl expression and grl-negative cells at the axial veins). Anteriorly, grl was expressed in the endothelial cells of the paired aortae, but not in the bilateral cardinal veins (FIG. 3E; transverse histological section of the anterior trunk showing grl expression at the paired dorsal aortae below the notochord). In the trunk, grl expression was detected in the midline aorta, but not in the axial vein (FIGS. 3F–3G; transverse histological sections of posterior trunk showing grl expression in endothelial cells at the midline dorsal aorta and the intersomitic artery, and no grl expression in the endothelial cells at the axial veins). By contrast, fli, an early endothelial marker, was expressed in both arteries and veins (FIGS. 3H–3I). At the anterior trunk, grl was expressed selectively at the region of aortic bifurcation, the region most affected by the grl mutation. In addition, grl is transiently expressed in the heart, aortic arches, and lateral somites, a pattern that is similar to that described for the mouse Hey and HRT genes (Leimeister et al., Mechanisms of Development 85:173–177, 1999).

Ectopic Expression of grl Rescues the grl Mutant

If the m145 mutation in the grl gene is responsible for the aortic dysmorphogenesis of the mutant zebrafish embryos, wild type grl RNA should be able to rescue the mutant phenotype.

To ascertain whether wild type grl can rescue the defect of the grl$^{m145}$ mutation, in vitro transcribed grl RNA, encoding either wild-type grl protein (grl$^{wt}$) or a mutant grl protein, truncated at amino acid 250 before the YRPW motif (grl$^{del}$) was microinjected into one- to four-cell stage wild type and mutant embryos from grl in-crosses. Different doses of mRNA were tested, and about 55 pg of mRNA was used for the injections. An average of 90% of the wild type embryos, injected with 55 pg of grl$^{wt}$ or grl$^{del}$, developed normally. A high dosage of mRNA (about 200 pg) caused developmental defects in about 60% of the wild type embryos. Sense-capped RNA was synthesized for injection using T7 RNA polymerase and the mMESSAGE mMACHINE system (Ambion) after HindIII digestion of wild type grl and a grl RNA having a C-terminal truncation. Injection was carried out using Microinjector 5242.

Microinjected embryos were scored based on the phenotype of the mutation and then genotyped. The $grl^{m145}$ mutation is a fully penetrant, recessive mutation and the most robust phenotype is the absence of angiographically demonstrable circulation to the trunk at 48 hours (FIGS. 4A–4B). Microangiography was carried out as described (Weinstein et al., *Nature Medicine* 1:1143–1147, 1995). Phenotypic analysis was carried out based on the condition of circulation at the trunk and tail and some of the embryos were analyzed by angiogram 48 hours after fertilization. The injected embryos were classified as phenotypically wild-type if they had normal tail circulation and mutant if they lacked tail circulation. All injected embryos were genotyped by a closely linked microsatellite marker; some of the genotyped embryos were further confirmed by sequence analysis.

FIGS. 4A–C show phenotypic complementation of the grl mutation by microangiography. FIG. 4A indicates the phenotype of wild type embryos, displaying blood flow to the trunk through the dorsal aorta (arrow) and its return via the axial vein (arrow). FIG. 4B shows the grl mutant with a lack of circulation in the trunk, due to the blockage at the aortic junction of the paired dorsal aortae. FIG. 4C shows a phenotypically wild type and genotypically mutant embryo in which circulation in the trunk was restored. The C-terminal nucleotide sequence of the grl is shown to the right in four wild type, four mutant, and four rescued embryos, respectively. The grl mutant embryos and the rescued grl mutant embryos have a T-to-A point mutation, compared to the wild type sequence.

As shown in Table 1 and FIGS. 4A–C, in clutches injected with wild type grl RNA, the predicted number of embryos manifesting the grl mutant phenotype was reduced by 26%. By contrast, a grl truncated mutant gene, in which the carboxyl terminal region is deleted, including the YRPW motif, as shown in Table 1, was not capable of rescuing the m145 mutation.

The apparently wild type, rescued embryos were confirmed to be genetically mutant by sequence analysis. The grl mutant embryos and the rescued grl mutant embryos had a T-to-A point mutation, compared with the wild type sequence.

As noted above, grl is a member of the hairy-related family of bHLH proteins, which are important for cell fate determination in other cell types. In the Drosophila nervous system, for example, members of the hairy family act downstream of Notch as transcriptional repressors, and help to pattern and establish equivalence groups of neural progenitor cells. Our studies show that grl could play a similar role specifically for aortic angioblasts, showing a role of bHLH genes in vasculogenesis.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it is to be understood that it is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the appended claims.

TABLE 1

Rescue of grl Mutants by RNA Injection

| Injected RNA | Total Embryos | Phenotypically Mutant Genotypically Mutant | Phenotypically Wild-type Genotypically Mutant |
|---|---|---|---|
| $grl^{wt}$ | 151 | 29 | 10 |
| $grl^{del}$ | 66 | 16 | 0 |

What is claimed is:

1. A substantially pure gridlock polypeptide, wherein said polypeptide comprises (i) a basic domain, (ii) a helix-loop-helix domain, (iii) an Orange domain, and (iv) a protein-protein interaction domain that comprises a YRPW motif, wherein the amino acid sequence of said polypeptide is at least 55% identical to the amino acid sequence of SEQ ID NO:2 or SEQ ID NO:4.

2. The polypeptide of claim 1, wherein said amino acid sequence is at least 60% identical to the amino acid sequence of SEQ ID NO:2 or SEQ ID NO:4.

3. The polypeptide of claim 1, wherein said amino acid sequence is at least 75% identical to the amino acid sequence of SEQ ID NO:2 or SEQ ID NO:4.

4. The polypeptide of claim 1, wherein said polypeptide is a mammalian polypeptide.

5. The polypeptide of claim 4, wherein said polypeptide is a human polypeptide.

6. The polypeptide of claim 1, wherein said amino acid sequence is at least 90% identical to the amino acid sequence of SEQ ID NO:2 or SEQ ID NO:4.

7. The polypeptide of claim 1, wherein said amino acid sequence comprises the amino acid sequence of SEQ ID NO:2 or SEQ ID NO:4.

* * * * *

UNITED STATES PATENT AND TRADEMARK OFFICE
CERTIFICATE OF CORRECTION

PATENT NO. : 6,558,932 B1 Page 1 of 1
APPLICATION NO. : 09/705534
DATED : May 6, 2003
INVENTOR(S) : Mark C. Fishman and Tao P. Zhong It is certified that error appears in the above-identified patent and that said Letters Patent is hereby corrected as shown below:

Column 9,
Line 5, replace "zebrafish" with -- human --; and
Line 6, replace "human" with -- zebrafish --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,558,932 B1 |
| APPLICATION NO. | : 09/705534 |
| DATED | : May 6, 2003 |
| INVENTOR(S) | : Mark C. Fishman and Tao P. Zhong |

Page 1 of 1

It is certified that error appears in the above-identified patent and that said Letters Patent is hereby corrected as shown below:

Column 27,
    Line 18, replace "SEQ ID NO:2" with --SEQ ID NO:4--; and
    Line 19, replace "SEQ ID NO:4" with --SEQ ID NO:2--.

Signed and Sealed this

Thirteenth Day of May, 2008

JON W. DUDAS
*Director of the United States Patent and Trademark Office*